(12) United States Patent
Cottingham et al.

(10) Patent No.: US 7,045,677 B2
(45) Date of Patent: May 16, 2006

(54) FUSION PROTEINS INCORPORATING LYSOZYME

(75) Inventors: Ian Robert Cottingham, Edinburgh (GB); Graham Edward McCreath, Edinburgh (GB)

(73) Assignee: Pharming Intellectual Property BV, Al Leiden (NL)

( * ) Notice: Subject to any disclaimer, the term of this patent is extended or adjusted under 35 U.S.C. 154(b) by 244 days.

(21) Appl. No.: 10/024,597

(22) Filed: Dec. 21, 2001

(65) Prior Publication Data

US 2003/0167477 A1    Sep. 4, 2003

Related U.S. Application Data

(63) Continuation of application No. 10/019,153, filed as application No. PCT/GB00/02459 on Jun. 23, 2000, now abandoned.

(60) Provisional application No. 60/147,819, filed on Aug. 10, 1999.

(30) Foreign Application Priority Data

Jun. 2, 2000    (GB) .................................... 9914733

(51) Int. Cl.
*A01K 67/27*    (2006.01)

(52) U.S. Cl. ............................ 800/14; 800/7; 800/15; 800/16; 800/17; 800/18

(58) Field of Classification Search .................... 800/7, 800/14–18; 536/23.2, 23.4
See application file for complete search history.

(56) References Cited

U.S. PATENT DOCUMENTS

| 5,322,775 | A |   | 6/1994  | Clark et al. ................ 435/69.1 |
| 5,366,894 | A |   | 11/1994 | Clark et al. .............. 435/320.1 |
| 5,476,995 | A |   | 12/1995 | Clark et al. .................... 800/2 |
| 5,610,053 | A |   | 3/1997  | Chung et al. ............ 435/172.3 |
| 5,620,923 | A |   | 4/1997  | Rechsteiner et al. ....... 435/69.7 |
| 5,650,503 | A |   | 7/1997  | Archibald et al. ......... 536/23.5 |
| 5,827,690 | A |   | 10/1998 | Meade et al. .............. 435/69.6 |
| 5,861,299 | A |   | 1/1999  | Archibald et al. ....... 435/240.2 |
| 5,993,809 | A | * | 11/1999 | Weaver et al. ........... 424/94.61 |
| 6,211,427 | B1 |  | 4/2001  | Cottingham et al. ........... 800/7 |

FOREIGN PATENT DOCUMENTS

| EP | 0 181 634 A2 | 5/1986 |
| EP | 0 590 530 A2 | 4/1994 |
| EP | 0 771 874 A2 | 5/1997 |
| WO | WO 88/00239 A1 | 1/1988 |
| WO | WO 90/05188 A1 | 5/1990 |
| WO | WO 92/11358 A1 | 7/1992 |
| WO | WO 92/22644 A1 | 12/1992 |
| WO | WO 93/25567 A1 | 12/1993 |
| WO | WO 94/04672 A1 | 3/1994 |
| WO | WO 95/27782 A1 | 10/1995 |
| WO | WO 97/07668 | 3/1997 |
| WO | WO 97/07669 | 3/1997 |
| WO | WO 97/42835 A1 | 11/1997 |
| WO | WO 00/29588 A1 | 5/2000 |

OTHER PUBLICATIONS

Akinbi et al., "Enhanced bacterial clearance in the airways of transgenic mice expressing a lysozyme/SP-B fusion protein," Amer. J. Respiratory and Crit. Care Med. 159 (3, Suppl. S): A752, Mar. 1999.*

Lee et al., "Expression of a bovine beta-casein/human lysozyme fusion gene in the mammasry gland of transgenic mice," J. Biochem. Mol. Biol. 31 (4): 413-417, Jul. 1998.*

Struck et al., "High concentrations of procalcitonin but not mature calcitonin in normal human milk," Horm. Metab. Res. 34: 460-465, 2002.*

Palmiter, R.D. et al., "Dramatic growth of mice that develop from eggs microinjected with metallothionein-growth hormone fusion genes," *Nature* 300:611-615, MacMillan Journals Ltd. (1982).

Maga, E.A. and Murray, J.D., "Mammary Gland Expression of Transgenes and the Potential for Altering the Properties of Milk," *Biotechnol.* 13:1452-1458, Nature Publishing Company. (Dec., 1995).

Brignon, G. and Ribadeau-Dumas, B., "A new method for human milk protein separation," *Biochimie* 64:231-235, Masson (1982).

Clark, A.J., et al., "Rescuing Transgene Expression by Co-Integration," *Bio/Technol.* 10:1450-1454, Nature Publishing Co. (1992).

Curtis, R.A., et al., "Protein-Protein and Protein-Salt Interactions in Aqueous Protein Solutions Containing Concentrated Electrolytes," *Biotechnol. Bioeng.* 57:11-21, John Wiley & Sons, Inc. (Jan. 1998).

During, K. "A Tightly Regulated System for Overproduction of Bacteriophage T4 Lysozyme in *Escherichia coli*," *Protein. Expr. Purif.* 4:412-416, Academic Press, Inc. (1993).

Eipper, B.A., et al., "The Biosynthesis of Neuropeptides: Peptide α-Amidation," *Annu. Rev. Neurosci.* 15:57-85, Annual Reviews Inc. (1992).

(Continued)

*Primary Examiner*—Scott D. Priebe
(74) *Attorney, Agent, or Firm*—Sterne, Kessler, Goldstein & Fox P.L.L.C.

(57) ABSTRACT

A process for the production of a peptide is disclosed, the process comprising expressing in the milk of a transgenic, non-human, placental mammal a fusion protein which comprises the peptide to be expressed linked to a fusion partner protein which is lysozyme. The fusion protein may be separate from the milk and cleaved to yield the target peptide. A transgenic, non-human, placental mammal whose genome incorporates a DNA molecule comprising a coding sequence encoding lysozyme coupled to a peptide is also described.

5 Claims, 12 Drawing Sheets

OTHER PUBLICATIONS

Eipper, B.A., et al., "Peptidylglycine α-amidating monooxygenase: A multifunctional protein with catalytic, processing, and routing domains," *Protein Sci.* 2:489-497, Cambridge University Press (1993).

Fischer, B., et al., "Physiological consequence of expression of soluble and active hen egg white lysozyme in *Escherichia coli*," *Appl. Microbiol. Biotechnol.* 39:537-540, Springer-Verlag (1993).

Goldman, A.S., et al., "Immunologic factors in human milk during the first year of lactation," *J. Pediatr.* 100:563-567, C.V. Mosby Co. (1982).

Han, K.-K., et al., "Current Developments in Chemical Cleavage of Proteins," *Int. J. Biochem.* 15:875-884, Pergamon Press Ltd. (1983).

Houdebine, L.-M., "Production of pharmaceutical proteins from transgenic animals," *J. Biotechnol.* 34:269-287, Elsevier Science B.V. (1994).

Ibrahimi, I.M., et al., "Determinants for protein translocation across mammalian endoplasmic reticulum. Membrane insertion of truncated and full-length prelysozyme molecules," *Eur. J. Biochem.* 155:571-576, Springer International (1986).

Jacquot, J., et al., "Identification of Different Molecular Forms of Human Airway Lysozyme," *Anal. Biochem.* 160:227-232, Academic Press, Inc. (1987).

Jespers, L., et al., "Overexpression of the phage lambda lysozyme cloned in *Escherichia coli*: use of a degenerative mixture of synthetic ribosome binding sites and increase of the protein stability in vivo," *Protein Eng.* 4:485-492, Oxford University Press (1991).

Lee, S.H. and de Boer, H.A., "Production of biomedical proteins in the milk of transgenic dairy cows: the state of the art," *J. Control. Rel.* 29:213-221, Elsevier Science B.V. (1994).

Lindahl, L., and Vogel, H.J., "Metal-Ion-Dependent Hydropohbic-Interaction Chromatography of α-Lactalbumins," *Anal. Biochem.* 140:394-402, Academic Press, Inc. (1984).

Lollike, K., et al., "Purification of Lysozyme from Human Neutrophils, and Development of an ELISA for Quantification in Cells and Plasma," *Leukemia* 9:206-209, Stockton Press (1995).

Lönnerdal, B., et al., "A longitudinal study of the protein, nitrogen, and lactose contents of human milk from Swedish well-nourished mothers," *Am. J. Clin. Nutr.* 29:1127-1133, American Society of Clinical Nutrition (1976).

McCreath, G.E., et al., "Preparation and use of ion-exchange chromatographic supports based on perfluoropolymers," *J. Chrom. A.* 773:73-83, Elsevier Science B.V. (1997).

McKee, C., et al., "Production of biologically active salmon calcitonin in the milk of transgenic rabbits," *Nature Biotechnol.* 16:647-651, Nature Publishing Co. (Jul. 1998).

Noppe, W., et al., "Simple two-step procedure for the preparation of highly active pure equine milk lysozyme," *J. Chrom. A* 719:327-331, Elsevier Science B.V. (1996).

Okun, M.M., et al., "Truncations of a Secretory Protein Define Minimum Lengths Required for Binding to Signal Recognition Particle and Translocation across the Endoplasmic Reticulum Membrane," *J. Biol. Chem.* 265:7478-7484, American Society for Biochemistry and Molecular Biology, Inc. (1990).

Paleyanda, R.K., et al., "Transgenic pigs produce functional human factor VIII in milk," *Nature Biotechnol.* 15:971-975, Nature Publishing Co. (1997).

Prasad, R.V., et al., "Amino Acid Sequence of Rat α-Lactalbumin: A Unique α-Lactalbumin," *Biochemistry* 21:1479-1482, American Chemical Society (1982).

Pursel, V.G., et al., "Genetic Engineering of Livestock," *Science* 244:1281-1288, American Association for the Advancement of Science (1989).

Pursel, V.G. and Rexroad, C.E. Jr., "Status of Research with Transgenic Farm Animals," *J. Anim. Sci.* 71:10-19, American Society of Animal Science (1993).

Ray, M.V.L., et al., "Production of Recombinant Salmon Calcitonin by In Vitro Amidation of an *Escherichia coli* Produced Precursor Peptide," *Bio/Technol.* 11:64-70, Nature Publishing Co. (1993).

Sloane, R.P., et al., "Expression and purification of a recombinant metal-binding T4 lysozyme fusion protein," *J. Biotechnol.* 49:231-238, Elsevier Science B.V. (1996).

Vachier, M.C., et al., "Isolation of hen egg white lysozyme, ovotransferrin and ovalbumin, using a quaternary ammonium bound to a highly crosslinked agarose matrix," *J. Chrom. B.* 664:201-210, Elsevier Science B.V. (1995).

Van Heeke, G., et al., "Gene Fusions with Human Carbonic Anhydrase II for Efficient Expression and Rapid Single-Step Recovery of Recombinant Proteins: Expression of the *Escherichia coli* $F_1$ -ATPase & Subunit," *Prot. Exp. Purif.* 4:265-274, Academic Press, Inc. (1993).

Vasstrand, E.N. and Jensen, H.B., "Affinity chromatography of human saliva lysozyme and effect of pH and ionic strength on lytic activity," *Scand. J. Dental Res.* 88:219-228, Munksgaard (1980).

Vilotte, J.-L., et al., "Efficient tissue-specific expression of bovine α-lactalbumin in transgenic mice," *Eur. J. Biochem.* 186:43-48, Springer International (1989).

Winters, M.A., et al., "Protein Purification with Vapor-Phase Carbon Dioxide," *Biotechnol. Bioeng.* 62:247-258, John Wiley & Sons, Inc. (Feb. 1999).

Wold, F., "In Vivo Chemical Modification of Proteins (Post-Translational Modification)," *Ann. Rev. Biochem.* 50:783-814, Annual Reviews, Inc. (1981).

Wright, G., et al., "High Level Expression of Active Human Alpha-l-Antitrypsin in the Milk of Transgenic Sheep," *Bio/Technol.* 9:830-834, Nature Publishing Co. (1991).

NCBI Entrez, Genbank Accession No. X14008, from Sippel, A.E., National Center for Biotechnology Information (1997).

Unverified English language abstract of EP 0 590 530 A2 (Document AN2), Derwent World Patent Index (Dialog File 351), Derwent WPI Acc. No. 94-111012/14, Derwent Info Ltd. (1997).

\* cited by examiner

FIG. 2A

```
AAGCTTGCATGCTGCAGGTGACCTGCAGGTCAACGGATCTCTGTCTGTTTCATGTTAGTACCACACTGTTTGGTGGCTGTAGCTTTCAGCTACA      100
GTCGAAGTCATAAGCCTGGTACCTCCAGCTCTGTTCTCTCTCAAGATTGTGTCTTGTCTTGGTCTTCAGTATAGTGTCTCCACACAATTTTAGAATGT  200
TGTTCTAGTTCTGTGAAAATGATGCTGGTATTTGATAAGGATTGCATTGAATCGTAAAGCTACAGATATAGTCATTGGTAGTACAGTCACTTTAA     300
CAATATTAACTCTTCACTCTGTGAGCATGATCATTCTGATAGTCTCCCCTCTATCACTCTTCAATTCCTCTATCAGTTTCTTCATTGCAGTTTCTGAGTAC 400
AGTCTTACACCTCCTTGGTTAGAGTCATTGCTTGATACAATTGTGAATGAGTAATTTCTTAGTTTCTTCTTCTTCTGATAGCTC                 500
ATGTTAGTGTATATATAGAAAAGCAACAGATTTCTATGTATTAATTTTGTATCCTGCAACAAGGTGTCATGTCATCTGCAAACAGTGGCA           600
GAATTCACTTATTAGCTTTTTGGTGACATCTGGATTTTCTGAGGATTTTCGTCTGAGTACGACTAGGATTCCCAATACTATACGAATAAAAGTGGCAAGAGTGG 700
GTTTCCTTCTTCCCTTCCAACCTGGATTTTTCTGACCTTAGAGGAAATGCTTTCAGTTTTCTTTATCATAAAAGTATTTGTCAAAAGTTTTTCCTGCATCTATTGAGATGAT 800
ACATCCTGTCTTATTTTCTGACTTAGAGGAAATGCTTTCAGTTTTCATCATAAAAGTATTTGTCAAAAGTTTTTCCTGCATCTATTGAGATGAT     900
TATGGAGGTCTATTCCCTCTGTTGAGAGTTTTTATCATGAGAAAGATCCACACCTTGTGAGAGTTTTTATCTTGGTAATCACATTGATTGTTGG     1000
TTTACTCTTCATTCATTATGATTTTTATTCTTCATTTGTTAATGATTTCCATTCTTCAATTGTTAACGTGGTATATCACATTGATTGTTGG        1100
ATACCTTTGTATCCTGGGATAAACCTCACTTGATCATGAGCTTTGTCTGGTTTAGTATCAGGGTGATGCTGGCTTCATAGACTGTCAGTCATCTT     1200
ATTCATCAATGATATTGGCCTAAGATGTTTGAGTAGGATAGTATTAACTCTTCTTTAAATGTTTGGGACTTCCCTGGTTGAGCCGGTGCAACATGTT 1300
ATTTTCGGAATAGTTTGAGTAGGATAGTATTAACTCTTCTTTAAATGTTTGGGACTTCCCTGGTTGAGCCGGTGCAACATGCTGAGCTGCAGTGCC   1400
GGGTTTGATCCCTGGTCAGGGACTGCACTTGCAGGAACCATTAATAAGATCTGCCTTCGACCTGCTTCTGGAAAAGAATTGCCCCCAGTCAGTGCC   1500
CACAGGCCACGAACCAGAGAAAGCCACATACAGAGGCCCAACCCAGCAGCACCAACCCAGAAAAGAGTTGGTGGAATACAGCTGTGAAGCCGTCTGGTCCT 1600
ATACCTTTGCTTGAGGGAATTTTTAAAATCTCACTTGATCATGAGCTTGATTGTCAATGTAACGGTCTGTTCATATTTCATTTCTTCCGGGTTCAGTCTTGG 1700
GAGATGTACATGCTAGGAGCTCCAGGCTGGCCCAAGCATGGTCATCTAGAGTGTGTGAAAGCAGGGTTTGGCAGGACGGGAGATGCTGAGAGCCGACGGGGTCA 1800
GCTTCCTGGGGCTGCAGGGCTGGCCAAGCATGGTCATCTAGAGTGTGTGAAAGCAGGGTTTGGCAGGACGGGAGATGCTGAGAGCCGACGGGGTCA   1900
GATTCCTGCTTCTGCACTTAGAGGCCAGGATCTGCACCTGCTTCTGGGAAAGATTGCCCAGTCAGTGCCAGCTGCCCAGCCAGAGCTG           2000
GGTCCCTCCCCAGGCCCGTCTGTCTGGATGGTTATTCTCGAAGGTTCCTGGAAGTTGAAGTTCCTGAAGGTCATGGCATGGTTTGTGGTCACG     2100
CTTATTCCGTCTCTCTGGAGACCCTGCAGCTCAGAGCGTCGCAGATTCCGAGAGTTCCGCCACCCAGAGTTCCTAAGCTCTGGTGCCACCAGGACGCGGTGTCCAAACCACCCGTGC 2200
GTCACAGGAACTTGGAGGACCTCCTCCTGCATCACCCAGTTGTCAGCTGCAGCCAGTTCCAGCAGCCGTCTGGGTGCTGGGGTCCTGGGTGTCCAAACCACCCGTGC 2300
GGCTGACCTTCGGGGCTACCATGGGAGGAGGGCTTCACACGCCTTCGCAAACCTGGGTTTATCGTAAACATGGAAGTTCCGAGTGTGAACTGGAAGATCC 2400
TGGTGTTCGGGGCTACCATGGGAGGAGGGCTTCACACGCCTTCGCAAACCTGGGTTTATCGTAAACATGGAAGTTCCGAGTGTGAACACTGGAAGATCCC 2500
GAGCCTCCTCCAGAGGGTCTCCAGGAGGGAGCCTTCACACGCCTTCTAAAGACCTAGAATGGAACCTGGGTTTATCGTAAACATGGAAGTTCCGAGTGTGACACTGGAGATT 2600
TCTAGTCTCTGCCTGAACAGCTCGTTCATCTCAGTTGCAGTTGCAGTTCATCGCAAATGGAACCTGAGTCGTCCTCTTCATCACAGGAAAGGGGCCTGAGGCTTGCAGTT 2700
CAGCCTGCTTGAACAGCTTCATCGCAGTTCATCGCAAATGGAACCTGAGTCGTCCTCTTCATCACAGGAAAGGGGCCTGAGGCTTGCAGGCTTGTTGCA 2800
AACCCATCATCACAGAGGTTCACACGTCTCGTAATACAGATCAGGCAAGGACTGAAGGACTGAAGCTGGTGAGTTCTGATGTGAAACACTGAGCTTCTGAGATTAGCCCTGTTC 2900
AGAATTAAGGTGCTAATACAGATCAGGCAAGGACTGAAGGACTGAAGCTGGTGAGTTCTGATGTGAAACACTGAGCTTCTGGGGGCTGAGGTCT   3000
GCTCCCGTGAGTGAGCTCTTTCCTGCTACAGTCACCAACAGTCTCTCTGGAAGGAAACCAGAGAGCCAAGCCGAGCTAGTTTAGGAGACCCC       3100
```

FIG. 2B

```
TGAACCTCCACCCAAGATGCTGACCAGGCCAGGCGGCCCCCTGGAAAGACCCTACAGTTCAGGGGGAAGAGGGGCTGACCGCCAGGTCCCTGCTATCA  3200
GGAGACATCCCCGCTATCAGGAGATTCCCCGTCCCTTGCTCCGTTCCCTATCCCAATGCCCACCCACCCTGTGATGAGCAGTTTAGTCACTTAGA  3300
ATGTCAACTGAAGGCTTTTGCATCCCCCTTTGCCAGAGGCACCACAAGGCACCTGCTGGGTACCGACGCCCATGTGGATTCAGCCAGGAGGCCTGTC  3400
CTGCACCCTCCCTGCTCGGGCCCCCTCTGTGCTCAGCAACACCACCAGGATTCCCGCTGCTCCTGAGGTCTGCCCATCCCACGTGCTGCATTAGC  3500
GCGGTGTGGAGGGAAGTGTCCTGCCCCCGTGCCGTGCTCAGCCAGGGTCAGTTTAAAATGTGAGAGGCGGGAGGTGGGCCTGTGGGCTGGGTTATTGACTCTTGTCATTGCCATTTTGCTACC  3600
CCCAGTGCTGCTCAGCCAGGTGCTTGCAGAGATCCCTTCACCCAAGGCACGGTCACATGGTTTGGAGGAGCTCGGAGGAGCTGTGCCCAAGCCAGAGGCAGAGGCCACCCTGCCCAGGACACACCCTGCC  3700
CTAACTGGGCTGACTGCAGAGATCCCTTCACCCAAGGCACGGTCACATGGTTTGGAGGAGCTCGGAGAGCTGTGCCCAAGCCAGAGGCAGAGGCCACCCTGCC  3800
GGTGGGTGCTGGCTCTGAGGGCTTGGGCTCTAGGCCACCGTCTAGGCCAACCGTCTAGGGGCCAGAGGTGTTCCTGGCACTGGCCCCAGAGTCCAGACACCTGT  3900
CCAGTGCTGGCTTCTGGGCTTCTGGGGCCTTGGGGCCTTCAGCCCTTCACCATCGATGGAAGCCCTCCTTGCATGCCTCCTGTAGGA  4000
GCCCCCGCTTCTGGGCGGGCCTGAGGATGAGCAGGCCAAGTGGGATTCCAGGGAACCGTCTAGGCCACCCGTTCACGTGCCTGGATGGAAGGCCTTGCCTGCATGCCTCCTGTATAAGG  4100
AGCACCCCGGGGCCTGTCTCAGCCCTCCACTCCCTGCAGAGCTCAGAGGCACGACGGCCAAGTCCCAGGGATCCTGCTAGCACTGCGACTAGCAGTCAACATGAAGGC  4200
CCCCAAGCCTGCTCTGGGGCCTTGTCCTCCTTTCTGTTACGGTCCAGGCGAGTTTGAGGTGGCCAGAACTCTGAAAGATTGGGAATGGAT  4300
TCTCATTGTTCTGGGGCCTTGTCCTCCTTTCTGTTACGGTCCAGGCGAGTTTGAGGTGGCCAGAACTCTGAAAGATTGGGAATGGAT  4400
GGCTACAGGGGAATCAGCCTAGCAAACTGTAAGCCTAAGCTAGTCCATAATTCCAGAGAATTAGCTAAAACATCAGTTTGGTTCTTTATAACCAGAGATACCCG  4500
GAAGGGCTTTGAGTGAATAGATCGGCATGGCAGGGGAAAATTCCATTCTAAGTAAAACAGGACCTCTGTTGTGCTGTGACTCCAGTGTTCCATTTTGAACTT  4600
ATAAAGGAATACGGGCATGAAGCTGACTGAAGTGTGTCGATGATGCAGTAGAGCAGTCTAGAGTAGCTAGGAGAGCCTGAGAGCGATGCAGTAGAGCAGTCTAGAGTAGCTAGGAGAGCCTGAGAGCGTAGTATTTATTATTATATTTAT  4700
CAATGGCACATGTAAGCTGACTGAAGTGTGTCGATGATGCAGTAGAGCAGTCTAGAGTAGCTAGGAGAGCCTGAGAGCGATGCAGTAGAGCAGTCTAGAGTAGCTAGGAGAGCCTGAGAGCGTAGTATTTATTATTATATTTAT  4800
GGGCTCTGAGAGCGTAGTAGTCTAGAGTAGTCTTGTTTTCAGATTCAGGTCAGGGTCAGGGTCAGGTGTACCAGGTGTGTACCACCACCAGGTGTACCAGGTGTGTACCACCACCAGGTGT  4900
TTTAAAGACAGTCTCACTGTGTGGCCCAGGCTGGAGTGCAGTGGCATGGCGAATCTCAGCTCACTGCAACCTCGCCCTTCGCCTTCGGGCTCAAGTGATTCTCCTGCCTGGCTCCTGAGTCCT  5000
TCAGCTTCTGAACTCCTGGCCTCAAGTGATCTGCCACCTCAGCCTCCCAAAGTGCTGGGATTACAGGCGTGAGCCACTGCACCCAGCCGACGATGGATTTT  5100
GGTCTTGAACTCCTGGCCTCAAGTGATCTGCCACCTCAGCCTCCCAAAGTGCTGGGATTACAGGCGTGAGCCACTGCACCCAGCCGACGATGGATTTT  5200
AACAGTGATGTTTTTAAGAATATTATTTATTCTACTCTGATTAACTATCTTTCATTTCTCCACACCCACACCTTCCCACACCCAATCAAGAATGCCAATGCAAAGTTATTTTATA  5300
CATGAAATGTTTATTATTTTATCTGATGTAATAATCTGATCTCTGTAGTTTCAGATTGAATTCAGATTCCAATAGCTATTTTGAATGAGTGAAGGGAT  5400
GTTAGTACATAGTGTCGATGTAATAATCTCTGTAGTTTCAGATTGAATTCAGATTCCAATAGCTATTTTGAATGAGTGAAGGGAT  5500
GAAATCACGGAATAGTCTTGTTTTCAGATTCTAACTGATATCCAAATTCACCTTTAGATATATTATAAGAAAATTCTATCAGAAAATTCCTTATGTTTT  5600
CTGATTAAAAAAGCATTTTTCCATCAGCTATCTGCTATGAAGCAATGAAGAAACATGTATTTAAAGTATGTATAGAAAGTATGTTACAAGAT  5700
TGCCTGAGGGATGGGAGCACGGGTAAAGCAATGAAGAAACATGTATTTAAAGTATGTATAGAAAGTATGTTACAAGAT  5800
GATTGCATTACAAAGGATTCTCTTACAAGTCCCTTATCTTACAAGATATAAGCTGTAAGCATGAAGAAATTCCTAACTATAAGTGTAATTTTAAACAACATCAG  5900
TAAAATAGAAGTAGCTAAGTAGAACTGATTTTGCTATAGAGTATAAGTGTAAGCATGAAGTCACTTAGTGTTGCTGTTTATTACTAAAATAAGTTTCTTTTTCAGGGATGTGTT  6000
TGGCCAAATGGGAGAGTGGTTACAACACGAGCTACAAATACAGCTGGAGACAGAAGCACTGATTATTCAGATCAATAGCGCTACTG  6100
GTGTAATGATGGCAAAACCCCAGGAGCAGTTAATGCCTGTCATTTATCCTGCAGTGGTAAGACAAGTTATTTGACCAATCTGGTTATACTTACAAGA  6200
```

FIG. 2C

```
ATTGAGACTCAATACAAATGAAAAGCCTTGAAAGGTTCATGAGGACCTAGAAAAACTACATCTCAACTTCCAGAAAGTCATTATTATTTCCTCATAA  6300
TTCCCTGAGTAAGAGAAATTTAAGAAGTGGTATCATAAAGGTTGATGTTTTAATATACAGAAGTTTCTGAATGTGACCTATTAATTTACTGTCAATGGC  6400
CTTACTGATGCTTTGTCCAGAACAATGCCATTGCTCCTGCTTACTTGGGATAATTAGTTGTATGGTCCTTTTCAATTGTTTTACTT  6500
TTTTTTATGAAATGTTCTAAATGTTCTATAGAGACATTAGTATATAAACAGCCACTTATGCCATTATGCCATTTAAAAGTGTTAACATTTTG  6600
CCATAGTTGCTTCTTCTATGCCTTTTTTTTGTTTTTTTGCTCAGAGTTTTTTGTTTTGGTTTGTTTATTTGAGACAGGGTCTCC  6700
TGTCCCCAGGCTGTAGTCAGTGGCACCATCACTGCCAGCTCACTGCAGCTCACTGCACAGCCTCCCAAGTAGCTGGGACTACAGGTGTGCACC  6800
ACCATGCCTGGCAATTTTGAAATTTTAGTACAGGCAAATTCTGTTGTTGCCAGGCTGGTCTTGAACTCCTGAGTTCAAGCAATCTTCCCACCTCAGC  6900
CTCCTTAAGCTGCTGGAATTACAGGCGTTAGCACTGTACCTGGCTACTGCTGAGAGACTTTAAGTGAATTAGGAACATGATATATTCCATTCTAAAT  7000
TCTTAGTTTACATCTTCAAAAATAAAAATAGAAATACCATGTGGAATCCTCAGTGTCAAAATATTGCAGAAATCTTGCAAAGTTGATATTATTAAATATTA  7100
TTGAACTGCATATAAAAGAACATTAATCTTATTTCTAAAATCCAGTTAATTAAAATTTATATATATTATAAAAATTGGTCATTAAATAAATAAATAGAAA  7200
AATTCCCAATAAGAACATTAAACACCCATAATCTTACTACCCAGAGGTTTATAACCATGGGTAAATTCTGGTATATTATTCTTCCAGAATGTATATCAATCATG  7300
ATACAAATAAGAAAAAAATATCATCATAAACCCACACATAAACCATGTAAATACTGTGCTTTGCAAAAATTAAATTGTTATTATACACGGCT  7400
TGTATGAATGTTAAATTAATTATCACACAAAATTATTGCATGTCAGCAAATACAAATCGGTTTTAATGATCTTTTGCTCCATTTCCAGATGAGCACTTAGGTTGTT  7500
TTACAATTTGCTCTTATCATCATTTAAAGAATGACTAGAATTTAATATTCTATAATTGAATATTCTATGATCCAATTGTTACTATTGAGCACTTAGGTTGTT  7600
CAAATCTGTATCATCATTTAAAGAATGCTATGAATGCTATAGAATAGCTTTTTGTATACATCTTGGGTGCATTCTATTCTTTATTCTTGGATAAATTTCATAATAGAACTGCTG  7700
TCCATTTTCCTCATAGTTGTGTTTTTACAGTGTAGTGGGCTTTAATCATTCATTTGTAATACTGTTGTTGGATAAATTTCATAATAGAACTGCTG  7800
AGTAAAATCACTAGGCTTCATTCATGCTGATGCTTAACAGTGGCAGTTAATGGGAGAGAATGAACCTAAACCTGTAGCAATATATGGACTCATAGAAATAATATCTTACCA  7900
AAGAAAAAATGCTTCATTCATGCTGATGCTTAACAGAAAAGCTGGCTAACCTCAAAGAGGGTGTCCGTGATCCACAAGGCATGCTAATGACCAAATGCAGCTTTGTGAGAAATAATATCTTACCA  8000
TTCTTTCCACAGCTAACATCGCTGATGCTAGCTGCTGTGCAAGAAAAGCTGGCTAACCTCAAAGAGGGTGTCCGTGATCCACAAGGCATGCTAATGACCAAATGCAGCTTTAAGTGTTTAAGGGAAAA  8100
TGCAAGATAACATCGCTGATGCTAGCTTGTGCAAGAAAAGCTGGCTGTGCAAGAGAGCAGACTTTAAACTGATCCAGAATCTTTTAATTATTTATATTGCAGCTTTCTAGAGTTTT  8200
CTATCTTACTCTGTTGATATACAATGAGAGCAGACTTTAACTGATCTTAACTGATCCAGAATCTTTTGAAATTCTTTTAGAATAAGTAGTGGGCCACGCCTGTAATCCCAGC  8300
TGATGTATTACCTACACATCTTGAAGAACAATCTTGTCATATCTCTGTCATATGAGGTCAGGAGTTCGAGACCAGCCTGGGCAACATGGTGAAACCCCATCTCTACTAAAATACAAAAAT  8400
AAGATGCTTCACACTTCAGCTGGAGCAGATGGATGCCTGTAATCCAGAGGCTCAGGAGGCTGAGGCAGGAGGATCGCTTGAACCTGGGAGGTTGCAGAGGATGCGC  8500
ACTTTGGGTGTGTGGCAGGTGCCTGTAATCCCAGCCACTCGGGAGGCTGAGGCTGAGGCTGAGGTTGCAGTGCTGCTGCTACAACGC  8600
TAGCTGGGACTACAGGCGCCTGGGCGCACGAGTGACTTTGCCTGTAATCCTCAAATAAATGGAATTCACTTGTGCTGCAACGC  8700
CATTGTACTTCAGCCTGCGGGACAGCGTCGATGGCAGGAGCGCACGAGTGACTTTGCCTCAAATAAATGCTGCTGCTACAACGC  8800
ACATTACTCAATCTTTATGTTCGGACATTCAATTCTATTGATAAATATTTGTTTCCCAAGGAGTGCAAGGTTGTCAGTGCTGCAGAGATGCGC  8900
AGCTGGGTCTATCTTACTATTTTATCTATTGATAATATTTGTTTCCCAAGGAGTGCAAGGTTGTCAGTGCTGCAGTATGCAGTATTACAATGCGACTACATACCTTC  9000
ACCATTTGCTTCATCTTTTCTACAGGGTGGCATGGAGGCGGAGGAAGCGCTAGCACATGCAGAGATGCAGTATTACAATGCGACAGCGCTGCAGGGAG  9100
GAGGAGGAGGCGGCAGCGCAGGCGGCGGAGGGGCGGAGGAAGGCCTAGCACATGCAGAGATGCAGTATTACAATGCGACAGCGCTGCAGCA  9200
```

FIG. 2D

```
CAAGCTGCAGACCTACCCTAGGACCAACACCGGCAGGCGGCACCCCTGGATAATCGATAAGCTTGGATCCCCTGCCGGTGCCTCTGGGGTAAGCTGCCTGC  9300
CCTGCCCCACGTCCTGGGCACACACATGGGTAGGGGTCTTGGTGGGCCTGGAGACCCCACATCAGGCCTGGGCCCCGTGAGAATGGCTGGAA  9400
GCTGGGGTCCCTGCTGGGAGCTGGCAGAGCTGGCTGGCCGCGTGCCCACTCTGTGGGGTGACCTGTCTGCGGCCTGTGTCCTCCTCCAGCTCC  9500
TTCCAGGCAGAGCAGGCTAAGGTGGAAGGTGAGGCTAGGCGGGAGCTGGCCCAGGCCCAGGAAGTGGGTAGGCGGGCCCTTCCCGAGGAGGGGTGTCCTGAACCA  9600
CCAGGCATGGAGAGGCTGGCAGGCTGGCAGGTGCCCAGGAATCACAGGGGAATCCCATGTCCATTCAGGGCCTTGGCTCTCCTGGGG  9700
ACAGACGAGTCACCACCGCCCCCCCATCAGGGGACTAGAAGGGACCAGGACTGCAGTGCACCCTTCCTGGGACCAGGCCCTCCAGGCCCTCCT  9800
GGGCTCCTGCTCTGGGCAGCTTCTCCTTCACCAATAAAGGCATAAACCTGTGTCTCCCTTCGAGTCTTTGCTGGACAACTGGGCGGTGGAGAAG  9900
TGGTGGGGAGGGAGTCTGGCTCAGGAGGATGACACGGGGCTGGGATCCAGGGGCTCTGCATCACACAGTCTGCCACACCCCAACCATCACTG  10000
CGGCTCTTTGAAACTTTCAGGAACCAGGAGGAGGACTCGGCAGAGACATCTGCCAGTCTCACTTGGAGTGTTCAGTGTTCAGTCAACTCGACAAGGACAG  10100
AAGTGGAAAATGGCTGTCTCTTAGTCTTCATGGATCTAATAATTGATATGAAAACTCAAGTTGCTCATGGATCAAATTATGCCCTTTATGAAATCCAGCCACTACT  10200
GTCGGTATCAAACTTCATGTACCCAAAACGCACTGATCTTTTCTGTCTAAATGAAATAAAAGAGATTTCCCAAGATAGAGGAGCTGGGCAAAAGAGGT  10300
CACAGTTGGAAGGAGACTTGTTCTGCACACACACCTGATCATCAACAGCAAGGAGATCATCATTGAAAGACCCAGTCATTTGGGTTTGGGTGACTCCAGGAGTGTTCATTGGAGGACTGATGT  10400
TGAAGCTGAAACTCCAATGCTTGGCCACCTGCTGAAAGACTGAGTGACTGAACTGAGCTGAACTGCATGATGGGGATTTTTAGATAATAAGAATAT  10500
ACAGAGAGGATGAAATGTGGTCACAAAGACTAGTGATACTTTATGCAAGAATACTGGAGTGGGTAGCCATTCCTCCCGACCCAGGGATCTGAACCGGCATCTCC  10600
GCGGTTTATGGGGTCACAAAGACTGAGTGACTGAACTGAGCTGAACTGCATGATGGGGATTTTTAGATAATAAGAATAT  10700
ACACATAACATAGTGTATACTCATATTTTATGCAAGAATACTGGAGTGGGTAGCCATTCCTCCCGACCCAGGGATCTGAACCGGCATCTCC  10800
TTCTTCTGTCCACAGAATTCTCCAGGCAAGAATACTGTGCCACCACTGTCTTTTGTGACCTGGGTAGAGCCCGTGTACTGTCCCACTTAATTCCCGCTGACCTTCAGGACTCCCGGGAACACCCTCAGGACTCCCCCGGCCCTGACCCACAGT  10900
CCTGCAGACAGACACCGGGATTCTTCCCGGCCTAGCCTGCTCTGCTCTTCAAGGCTCATTATCTCATTATCTCAGGAGCCAGCCTTCAGGGTCATTCTTGTGACTTCGCTGCCGTAACTTCTGAACATCCA  11000
GTGCCGATGGACAGCCTCCTCCCCAGGCCTTCAGGGCTTCAAGAGAGCAAGACCAATGACTCTTCACCATGAGTCACCAGAACCAGACAAGCAGCCTACTTGCCCCTCAAGAACTGGACAAAAACCTTGGTGGGGAAGTTT  11100
CTCACAGTCTTCCCATCGTCCTGATCAAGAGAGCAAGACCAATGACTCTTCACCATGAGTCACCAGAACCAGACAAGCAGCCTACTTGCCCCTCAAGAACTGGACAAAAACCTTGGTGGGGAAGTTT  11200
CCTTTGAACCTAAAGACACCGGTGGCACCATCCTGCTTTGACCACCTGCTTTGACCACCTCGAAGGCCACCGAAGGTTTCTAATCTGACCGCACCCTGAATTAAGGCTGCACACCCGAATTAAGGCTGCACACCCTGAATTAAGGCTGCACACCCTGAATTAAGGCTGCACACC  11300
CAGGACACAGCCTGGTGCTCAACATCCGTGGCACCATCCTGCTTTGACCACCTGCTTTGACCACCTCGAAGGCCACCGAAGGTTTCTAATCTGACCGCACCCTGAATTAAGGCTGCACACC  11400
CATCCCAGAGGCTCAACATCCTGCTTTGACCACCTGCTTTGACCACCTCGAAGGCCACCGAAGGTTTCTAATCTGACCGCACCCTGAATTAAGGCTGCACACC  11500
TTTTGGCTGTGCTCAGCCTAAAGCTTTTTCCCCGTATCCCGGCTGCCCGGCTCGGGGGATGCCGGAGCGGCGACCGGAGGCGTCAAAGAGCAGCGGTTCAGAGAGGAAGCGTTCAGAGAGGAAGCGT  11600
CGCGTTCAGCAGCCTAAAGCTTTTTCCCCGTATCCCGGCTGCCCGGCTCGGGGGATGCCGGAGCGGCGACCGGAGGCGTCAAAGAGCAGCGGTTCAGAGAGGAAGCGT  11700
CCCCGTGCCGGGGCTCCGCACGCTGCCCGGCTCGGGGGATGCCGGAGCGGCGACCGGAGGCGTCAAAGAGCAGCGGTTCAGAGAGGAAGCGT  11800
GAGGGACGTAATTACATCCCTTGGGGGGGCTTTGGGGGGGCTGTCCCTGCGGGCCCGAATTC 12061
```

FIG.3.
milk
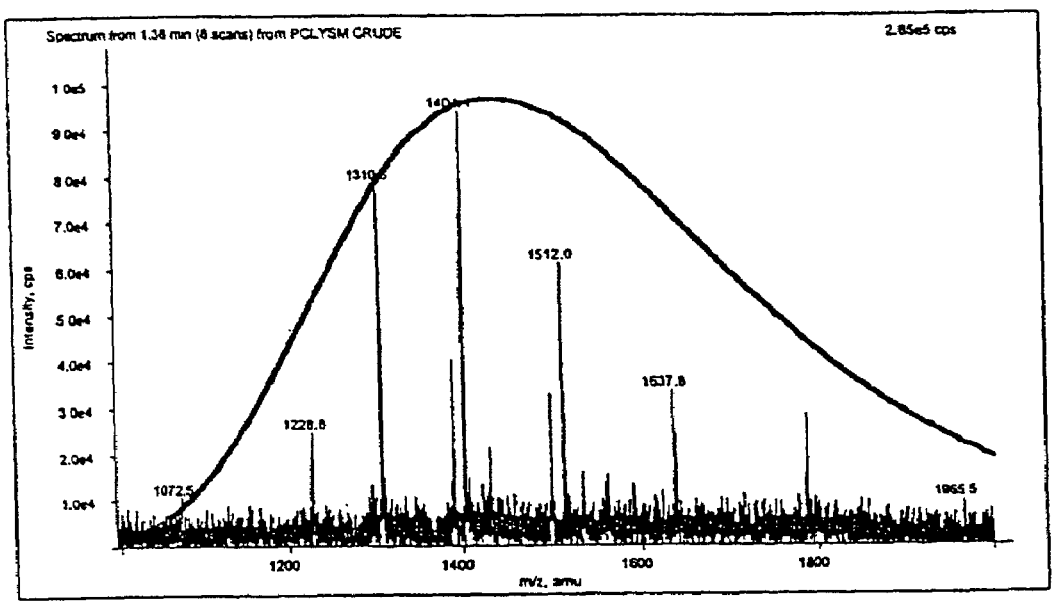
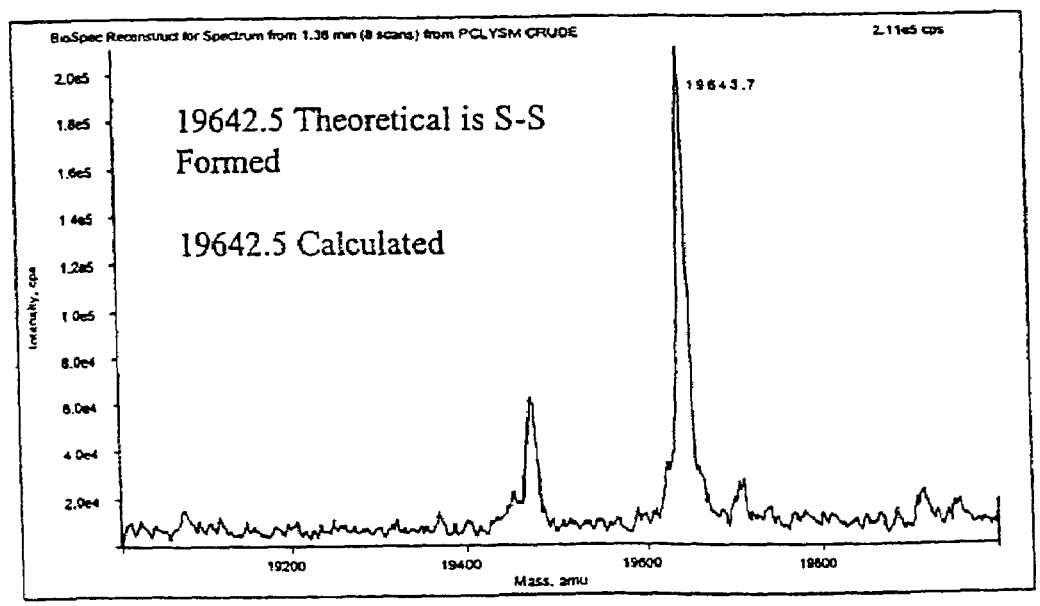
19642.5 Theoretical is S-S Formed
19642.5 Calculated lysozyme    linker    DDDK    GLP7-36    Glycine 1  2  3  4  5  6  7   8  9  10 11 12   13

Hlys Ab            GLP-1 Mab 1   2   3   4   5   6   7   8   9   10

FIG. 8.
8A
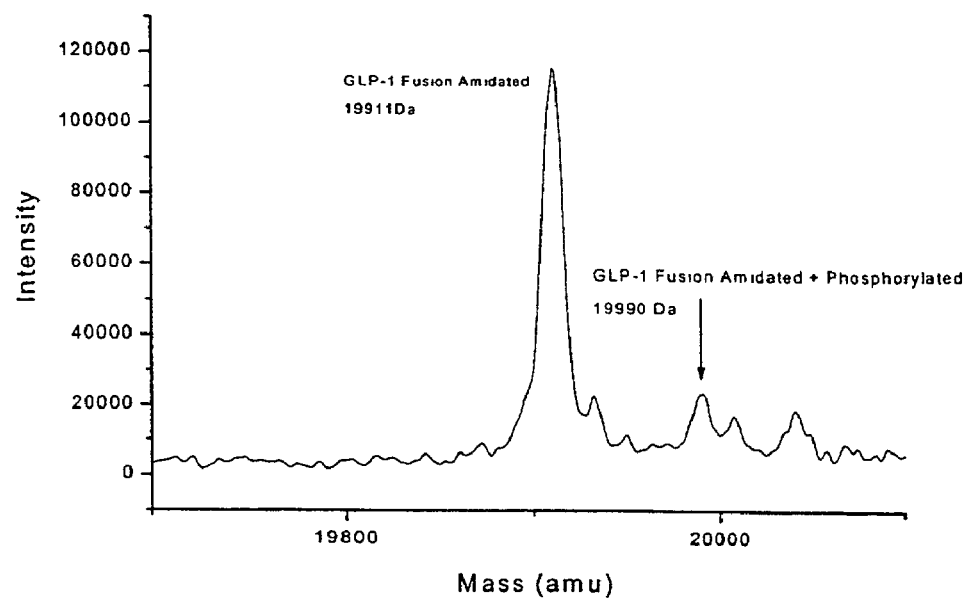
8B
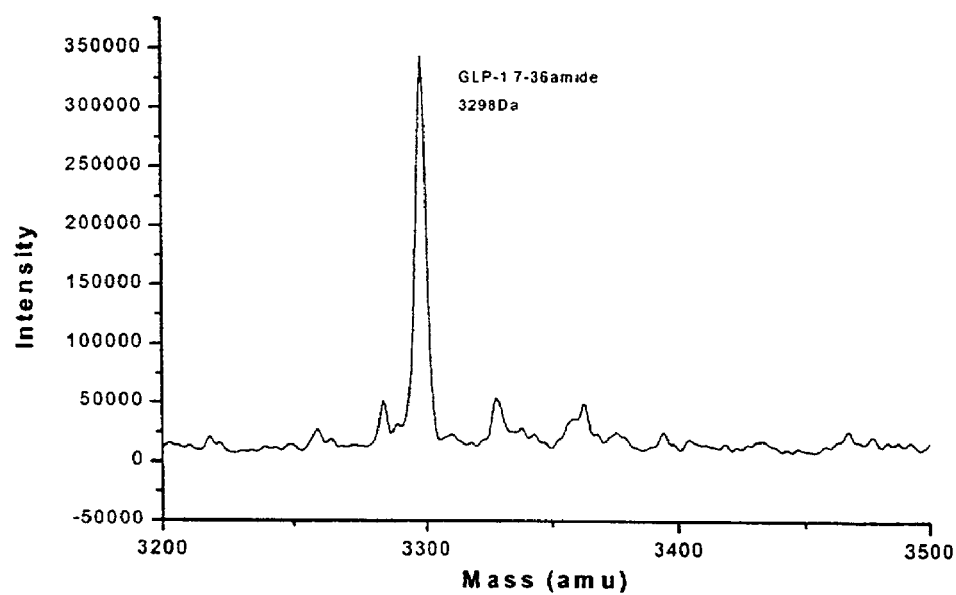

1  2  3  4  5  6

Fusion protein 1  2  3     4  5

FUSION PROTEINS INCORPORATING LYSOZYME

CROSS REFERENCE TO RELATED APPLICATIONS

The present application is a continuation of International Application No. PCT/GB00/02459, filed internationally on Jun. 23, 2000, which was published in the English language under PCT Article 21(2) as WO 01/00855 on Jan. 4, 2001, which entered the U.S. National Phase as U.S. application Ser. No. 10/019,153, on Dec. 21, 2001 (now abandoned), which claims the benefit of U.S. Provisional Application No. 60/147,819, filed Aug. 10, 1999, and which claims priority to GB Application No. 9914733.2, filed June 23, 1999, the disclosures of all of which are incorporated herein by reference in their entireties.

BACKGROUND OF THE INVENTION

1. Field of the Invention

The present invention relates to the production of peptides in the milk of transgenic mammals, for example non-human placental mammals.

2. Related Art

Polymers of amino acids concatenated via their amino and carboxyl groups form the basis for a variety of important biological compounds. Polymers of 3 to 100 amino acids are generally known as peptides, whilst larger polymers are known as proteins. This distinction is purely arbitrary, and polymers of up to about 110 amino acids can still be considered as "peptides". Thus, the term "peptide" as used herein refers to amino acid polymers of 3 to 110 amino acids. Peptides as defined herein may be biologically active without requiring any further modification, or may form the building blocks for larger complex molecules by chemical modification into larger structures or by modification such as glycosylation. The term "peptide" is used herein to include biologically active and inactive polymers, which may or may not have undergone further modification.

Peptides have a number of commercial applications, including use as medicaments, nutritional additives and research tools. For this reason, economic, large scale production of peptides is desirable. Direct chemical synthesis of peptides is expensive due to the high cost of reagents and the degree of purification needed to remove failed sequences. Microbial synthesis by recombinant DNA technology is an alternative, but not always appropriate for peptide production due to difficulties in extraction and purification from microbial cells, and the absence of microbial enzymes to perform necessary post-translational modification. Heterologous proteins may be produced in stably transfected mammalian host cell lines, many of which are commercially available today. However, concern remains that these cell lines are derived from tumours of various types.

As an alternative to the above methods, the production of proteins in the milk of transgenic sheep is possible, as illustrated in WO-A-8800239 and WO-A-9005188. The production of proteins in the milk of transgenic animals has the advantage that large volumes of milk containing the desired protein can be harvested using simple and environmentally safe technology. The use of living organisms to produce proteins means that all the material produced will be identical to the natural product. In terms of amino acid structures, this means that only L isomers will be produced. Also, the number of wrong sequences will be minimised due to the high fidelity of biological synthesis compared to synthetic routes.

Further, the use of a biological process for the production of the proteins ensures that only biologically safe materials are produced, in contrast to chemical methods where side reactions may produce toxic materials, which can only be removed at additional cost. The use of a biological process also enables some reactions, which are difficult to perform in good yield by chemical means, to be efficiently carried out. For example, carboxy terminal amidation of a peptide can be essential for biological activity or for the prolongation of in vivo half-life, and is carried out by a specific enzyme which recognises and modifies proteins having a glycine residue at the carboxy terminus (Eipper B. A et al., (1993) *Protein Science* 2 489–497). Therefore, suitably designed proteins produced by means of a transgenic animal will be specifically amidated prior to secretion. The amidation of proteins is only one of a number of post-translational modifications which can be carried out by the biosynthetic pathways in the mammary gland and harnessed for the synthesis of biologically active proteins. Other post-translational modifications include disulphide bridge formation, phosphorylation and γ-carboxylation of glutamic acid residues and the addition of O- and N-linked glycosylation (Wold, F. *Ann. Rev. Biochem.* 50 783–814).

The technology for the production of large proteins, as opposed to shorter peptides, in large quantities in the milk of transgenic sheep has been well established. For example, the human protease inhibitor, $\alpha_1$-antitrypsin has been produced in the milk of transgenic sheep in excess of thirty grams of protein per liter (Wright, G. et al., (1991) *Bio/Technology*, 9 77–84). It is expected that the same technology can be applied to the production of proteins in cattle, which can produce up to 10,000 liters of milk per lactation.

There are a number of difficulties relating to the secretion of short peptides in mammalian systems due to the nature of the secretory process. Proteins destined for secretion are directed into the endoplasmic recticulum, which forms the first stage of the constitutive secretory pathway, by a short pro-sequence, usually of at least twenty amino acids. The messenger RNA encoding a protein destined for secretion is translated by a ribosome which is initially free in the cytoplasm of the producing cell. However, as the end of the newly synthesised protein emerges from the large ribosome complex, the secretory leader sequence is bound to a 'signal recognition protein' (SRP). The act of binding has two effects. First, it causes the translation and protein synthetic machinery of the ribosome to 'pause' and secondly, it promotes the docking of the ribosome to the surface of the ER. This docking then re-starts translation and the protein destined for secretion is then synthesised through the ER membrane into the inner compartment. During the course of this second synthetic phase, the secretory leader sequence is cleaved off and the protein is folded appropriately. Then, after removal of the secretory leader sequence, and any secondary sequence related to correct folding, by proteolysis, and any other necessary modifications (primary glycosylation events, gamma carboxylation, etc) the protein moves on through the secretory pathway.

The fundamental problem with the secretion of peptides from mammalian systems is the requirement for a secretory leader sequence, the binding of the signal recognition peptide and the geometry of the ribosomal complex. Simple experiments have shown that if ribosomes which are actively translating proteins are treated with a powerful and non-specific protease, which can degrade all exposed proteins, then sequences of polypeptide about forty amino acids in length are protected. This implies that this sequence is buried within the large ribosomal complex and that only longer sequences capable of binding the SRP will be competent to enter the ER secretory pathway.

The requirement for a minimum peptide length was confirmed by studies which truncated normally secreted proteins such as lysozyme (Ibramimi et al (1986) Eur. J. Biochem 155(3) 571–6) and insulin (Okun et al (1990) J. Biol Chem. 265(13) 7478–84). Shorter versions of lysozyme, which still contained the secretory leader sequence, of 102 and 74 amino acids, were still capable of binding the SRP (as demonstrated by the ability of added SRP to 'pause' translation in a cell-free system) but a 52 amino acid truncation could not. Also, studies on the secretion of truncated insulin confirmed that not only did short peptides not 'reach' the SRP but were also secreted with low efficiency. Therefore, due to the basic mechanism of secretion it is evident that very short peptides cannot enter the secretory pathway. It is also apparent that even if peptides are long enough, with the addition of the secretory leader sequence, to engage the SRP, efficient secretion is unlikely due to a preference for amino acid sequences in excess of perhaps 100 amino acids (Okun et al (1990) J. Biol Chem. 265(13) 7478–84). This preference is reflected by the general size of secreted proteins which are normally at least 120 or more amino acids in length. Secretion of peptides shorter than 100 amino acids normally occurs via an entirely different mechanism where peptides are generated by the proteolytic cleavage of larger precurser proteins, sequestered in specialised vesicles within a cell and stored until needed. In this case secretion occurs in response to a specific signal which promotes fusion of the vesicle with the plasma membrane of the cell with concomitant release of the peptide into the external medium.

Thus, the basic mechanism by which proteins are secreted, involving ER docking mediated by the SRP, precludes the secretion of very short peptides, of less than perhaps 40 amino acids, and severely decreases the efficiency of peptides less than 100 amino acids long. In the absence of a fusion partner, to direct peptides to the secretory pathway, peptides of less than 100 amino acids long are naturally secreted by a completely different vesicle-based mechanism that only operates at high capacity in specialised tissues such as neurones. This pathway does not represent a viable alternative for making peptides in mammary tissue.

A second reason for expressing peptides as fusion proteins in milk is that it is easier to purify a fusion protein from milk, which is a complex biological fluid containing fats, sugars and proteins as well as peptides and proteolytic fragments, than to purify the free peptide. If the properties of the fusion partner dominate those of the peptide, it is likely that at least the initial purification steps will be common to processes for different peptides and thereby reduce development costs for a number of peptides. Regarding purification, the use of a peptide fusion is also beneficial in that two different recovery modalities can be employed: one for the fusion protein and then, after cleavage, one for the peptide. This approach is expected to yield a more pure product, or require fewer stages to achieve higher purity, because peptide impurities will be reduced during the purification of the fusion and protein impurities during the purification of the peptide.

The third advantage of expressing a peptide in milk as a fusion rather than as the peptide is that the biological properties of the pepide are likely to be masked and therefore not interfere with the physiology of the host animal. This has been demonstrated for calcitonin where it was shown that the alpha lactalbumin fusion protein was inactive in an in vivo assay designed to measure the depression of plasma calcium levels in the rat in response to an injection. This is in contrast to the cleaved and purified calcitonin which did exhibit biological activity (WO95/27782 and McKee C. et al (1998) Nat. Biotechnol.

The expression of heterologous proteins in mature or fused form in the milk of a transgenic female animal is also described in WO92/22644. This application discloses fusing a peptide gene sequence into a HINDIII restriction enzyme site in the coding sequence of the WAP gene, in order to express the peptide in milk. This fused gene construct merely serves to target the peptide expression to milk, but does not result in the expression of a fusion protein in milk, and thus is likely to suffer from the above mentioned problems of the art.

WO 95/27782 describes processes for the production of peptides in the milk of transgenic animals based on expressing the peptide linked to a "fusion partner protein". The fusion protein can be isolated from the milk and subsequently cleaved to release the desired peptide. In a preferred embodiment the use of human α-lactalbumin as a fusion partner protein linked to calcitonin as the desired peptide, is described. Human α-lactalbumin is a small, natural milk protein capable of terminal extension, thus satisfying some criteria of a fusion partner protein. However, it has demonstrated that human α-lactalbumin fusion constructs are expressed in the milk of rabbits at only 2.1 mg/ml (PCT/GB95/00769; McKee C. et al (1998) Nat. Biotechnol. 16(7) 647–651), a low yield compared to the yield of non-fusion $\alpha_1$-antitrypsin at 30 grams per liter. It is to this problem of low expression of such fusion proteins that the present invention is addressed.

BRIEF SUMMARY OF THE INVENTION

Thus, in a first aspect of the present invention there is provided a process for the production of a peptide, the process comprising expressing in the milk of a transgenic non-human placental mammal a fusion protein comprising the peptide to be expressed linked to a fusion partner protein which is lysozyme. Suitably, the process also includes the steps of separating the fusion protein from the milk, and cleaving the fusion protein to yield the peptide.

Lysozyme is a natural milk protein. It has been found to satisfy all the essential criteria of an ideal fusion partner protein whilst, surprisingly, enabling high yields of peptide compared to those achieved with other natural, milk-derived fusion partner proteins. Lysozyme is a small molecule of approximately 14,000 Daltons mass and containing about 120 amino acids, depending on the species. Therefore, the mass yield of peptide linked to lysozyme as the fusion partner protein will be high per mole of fusion protein produced. Due to its untypically high content of basic amino acids, lysozyme is simple and inexpensive to purify from expression media, such as milk. A further desirable feature of lysozyme, and an essential feature of any fusion partner protein, is its ability to carry an amino- or carboxy-terminal extension without any substantial effect on expression level or structural stability.

Lysozyme (EC 3.2.1.7) is a naturally occurring protein, secreted into bodily fluids, such as milk, saliva and airway secretions of a number of eukaryotic and prokaryotic species. Lysozymes are 1,4-β-N-acetylmuramidases which act as anti-bacterial agents by hydrolyzing the glycoside bond between the C-1 of N-acetylmuramic acid and the C4 of N-acetlyglucosamine in bacterial peptidoglycan. As mentioned above, these enzymes are small ($M_r$ 14,000–15,000) and basic in nature (pH 9.5–11). Lysozymes have been widely studied, as is apparent from hen egg white lysozyme which was the first protein containing all of the 20 common amino acids to be sequenced, the first enzyme for which a 3-D model was deduced by X-ray crystallography and the first enzyme for which a detailed mechanism of action was provided (Fischer et al., (1993), *Applied. Microbiology. and Biotechnology.* 39:537–540).

The lysozyme fusion partner protein of the present invention may be from any mammal which naturally secretes lysozyme in bodily fluids. The preferred lysozymes are those which are expressed at more than 5 g/l in the milk of transgenic animals and are stable with carboxy terminal extensions. Preferably, the lysozyme is that of a placental mammal, for example humans, cattle, sheep, goats, rabbits and rats. The lysozyme of other animals, such as chickens, may also be useful. It is also desirable that the genomic DNA functions well behind the beta-lactoglobulin promoter and is stable when built into DNA constructs.

DETAILED DESCRIPTION OF THE INVENTION

The present invention is based upon the surprising observation that much higher levels of expression can be achieved by using lysozyme as a fusion partner protein than, for example, α-lactalbumin, a small protein related to lysozyme with respect to sequence and disulphide bridges. The effectiveness of lysozyme in the expression system of the invention is seen, not only in terms of the absolute expression level of fusion protein, which is forty fold higher than that observed with α-lactalbumin, but also in the increase in the proportion of animals expressing fusion proteins at high levels. This latter observation has the surprising advantage that less $G_0$ founder animals are needed to generate a high expressing transgenic line. Although there is a possibility that generating and screening hundreds of α-lactalbumin founders would eventually give high expression levels, this is not viable commercially, especially since large animals such as cattle, sheeps and goats which are preferred for the present invention, are expensive to generate. Indeed, in view of the much higher expression levels achieved with the lysozyme fusion protein, and the inclusion of an 'insulator' to moderate integration position effects, it seems unlikely such expression levels could ever be achieved with the α-lactalbumin fusion protein.

The improvement in expression of the fusion protein with lysozyme over α-lactalbumin is observed in experiments where both DNA fusion constructs use the β-lactoglobulin promoter driving genomic constructs, thus excluding the possibility that the higher expression levels are attributable to differences in regulatory sequences. Likewise, in similar experiments, drastically improved expression was seen with lysozyme over α-lactalbumin, even after the inclusion in each construct of an 'insulator' sequence which is designed to isolate an integrated transgene, or transgene array, from effects of 'position' within the host genome (U.S. Pat. No. 5,610,053). Further experiments have shown that the lysozyme fusion protein expression is superior even when there is no difference in target peptide or cleavage site between the fusion proteins.

As mentioned above, lysozyme as a fusion partner protein is expressed at a higher level but, as importantly, the expression is consistently high for a number of transgenic lines. For instance, as seen in Example 1 the level of expression for the lysozyme-cyanogen bromide-calcitonin fusion protein in mice is 4.3±3.5 (n=19) with the highest level being 11.0 mg/ml, in contrast to the α-lactalbumin-cyanogen bromide-β-lactoglobulin construct where the average expression level is much lower, at only 0.16±0.10 (n=12), with the highest level being 0.26 mg/ml. Although there is not necessarily a direct correlation between the number of copies of a transgene integrated into the host genome and the resulting expression level, because of the very strong effect of integration site on expression, the disparity in expression between the two fusion partners cannot be attributed to poor integration of the α-lactalbumin construct. Copy number measurements for the above examples for expression levels in mice show that the copy numbers are between 5 and 30 copies for at least half of the lines analysed with either of the fusion partners.

Part of the rationale for using a fusion partner is that the expression level of the target peptide should be less dependent on the properties of the individual peptide. It is therefore expected that high level expression and high frequency of good expression seen with lysozyme should extend to any peptide. This is confirmed by experiments in mice using a lysozyme fusion with peptide GLP-1. Here, the same high expression lines and frequency of high expressing levels were seen in agreement with the results for the lysozyme-calcitonin fusion. The average expression level in mice was 15.4±5.4 (n=4) with the highest level being over 22.9 mg/ml. These results surprisingly show an even greater improvement over the results with calcitonin even though less animal lines were analysed.

The unexpected high level expression levels associated with the lysozyme fusion protein is not limited to particular transgenic species. Rather, the high expression levels seen in mice, compared to α-lactalbumin fusion proteins, is also seen in rabbits. As previously described, the enterokinase cleavable α-actalbumin-calcitonin fusion protein was expressed in rabbit milk at 1.55±0.45 mg/ml (n=3) with a maximum level of 2.1 mg/ml. In contrast, the lysozyme-GLP-1 fusion, again with the enterokinase cleavable linker, was expressed at 12.2±9.3 mg/ml (n=9) in rabbit milk, with a maximum expression level of 31.0 mg/ml.

The difference in expression efficiencies between lysozyme and α-lactalbumin is unexpected, in light of previous work on transgenic expression. A published report of bovine-lactalbumin expression from a cDNA in mouse milk gives an expression level of 0.45 mg/ml. (Vilotte, J. L. et al, (1989) *Eur J Biochem* December 8; 186 (1–2): 43–48). This allows a direct comparison with the expression of a human lysozyme cDNA construct expressed in mouse milk when the maximum expression was 0.71 mg/ml (Maga, E. A. et al, (1995)) and supports the premise that there is no intrinsic property in either molecule which predisposes a comparatively high expression level of lysozyme over α-lactalbumin.

In the fusion protein expression studies, both the lysozyme and α-lactalbumin genomic sequence constructs are driven by the same β-lactoglobulin promoter and carry the same 3' untranslated region, also from the β-lactoglobulin gene. A second possible explanation for the high lysozyme expression levels is that there is some factor, for example an enhancer of transcription, which is present within the genomic lysozyme sequence, which is absent from that of α-lactalbumin. If this were so, it would be predicted that the same comparatively higher lysozyme levels would be seen in natural human milk when compared to the levels of α-lactalbumin. This is not the case and, in fact, higher levels of α-lactalbumin (about 3 grams per liter of milk) are observed (Lonnerdal B et al. (1976) *Am. J. Clin.*

Nutr. 29(10) 1127–1133) compared to lysozyme (0.25 grams per liter) (Goldman A. S et al. (1982) *J. Pediatr.* 100(4) 563–7).

Thus, there is no evidence, from either expression studies of cDNA of lysozyme or -lactalbumin in transgenic milk or from the behaviour of the regulatory sequences driving expression in milk, to suggest that the expression level for lysozyme would be substantially higher than that of β-lactalbumin when both are expressed off genomic constructs using the same promoter and 3' environments.

Peptides produced by the present invention are preferably from 3 to 110, preferably 3 to 100 amino acids in length, but the invention is not limited to the production of peptides of the preferred range. The invention is particularly suitable for producing peptides which require post-translational modification in order to be biologically active, or improve in vivo half life, for example α-amidation. Many peptides found in the nervous and endocrine system of animals and bioactive peptides from other sources which have actions on the nervous system are -amidated. Examples include:

| | α-amidated residue |
|---|---|
| A alanine | b, o CRH; p Galanin; μ-Conotoxin |
| C cysteine | crustacean cardioactive peptide; conotoxins G1, M1, S1 |
| D aspartic | deltorphin |
| E glutamic | joining peptide |
| F phenylalanine | FMRF-NH$_2$; gastrin; cholecystokinin; CGRP; γ$_1$MSH |
| G glycine | oxytocin; vasopressin; GnRH; pancreastatin; leucokinin I, II; Manduca adipokinetic hormone; leucokinin I, II |
| H histidine | Apamin; scorpion toxin II |
| I isoleucine | h, r CRH; PHI; Manduca diuretic hormone; rat neuropeptide EI (melanin concentrating hormone) |
| K lysine | ELH; cecropin A; PACAP38$^a$, conotoxin GIA |
| L leucine | b, h GHRH; b-amidorphin; mastoparan; cecropin B; buccalin; myomodulin; PACAP27; proglucagon (111–123) |
| M methionine | Substance P; Substance K; PHM; gastrin releasing peptide; neurokinin A, B; neuromedin B, C |
| N asparagine | VIP (mammalian); neuromedin U; corazonin; mast cell degranulating peptide |
| P proline | calcitonin; TRH |
| Q glutamine | melittin; levitide |
| R arginine | preproglucagon (89–118) |
| S serine | frog granuliberin-R |
| T threonine | rat galanin; avian VIP; locust adipokinetic hormone |
| V valine | αMSH; r, p, h secretin; metorphamide/adrenorphin |
| W tryptophan | cockroach myoactive peptide, sea anemone peptide; crustacean erythrophore concentrating peptide |
| Y tyrosine | NPY; PYY; PP; ω-conotoxin; amylin |

$^a$PACAP, pituitary adenylate cyclase activating peptide.

An example of a biologically active peptide which is of medical and commercial interest is calcitonin. Other examples of peptides include parathyroid hormone, glucagon, glucagon-like-peptide-1, and members of the general classes of peptide: magainins, histatins, protegrins and clavainins. Calcitonin, for example, is a 32 amino acid peptide which contains a single disulphide bridge and is amidated at the carboxy terminus. The peptide hormone is secreted by the thyroid or parathyroid gland in mammals and by the ultimobranchial bodies in other vertebrates and serves to lower the level of calcium in the blood by reducing the level of release of calcium from bone. It is a highly functionally conserved molecule, and the protein obtained from salmon has widespread therapeutic applications for example in the treatment of Paget's disease, hypercalceamic shock and osteoporosis.

Another peptide of potential commercial interest is glucagon-like-peptide-1 (GLP-1). This is a 30 amino acid carboxy-terminal amidated peptide which is secreted by both gut cells and within the hypothalamus in response to feeding. Its main action is to potentiate the glucose stimulation of insulin secretion and to help regulate gastric emptying. It is therefore being evaluated as a potential therapy in the treatment of diabetes.

In addition to the above examples of specific peptides, there is an entire class of peptides that have anti-microbial activity, which will be required in large quantities and are therefore especially suitable candidates for production using the transgenic fusion protein approach. These peptides work by disrupting biologically important membranes usually by the creation of ion-permeant pores. Many of these are amidated and this modification possibly functions to increase biological half-life, by preventing degradation by carboxy peptidaces, and may also be important in reducing the net negative charge of the peptide, by modifying the acidic carboxylic group. Examples of antimicrobial and cytotoxic peptides include those belonging to the classes magainins, histatins, protegrins and clavainins.

A fusion protein produced by the above noted methods forms a second aspect of the invention.

When lysozyme is used as a fusion partner protein, it may be appropriate to add to the carboxy-terminus an extension which serves as a linker to join the fusion partner protein to the peptide. The linker is at least 10, 15 or preferably at least 20 amino acids in length. This is the first demonstration that a large (greater than 20 amino acids) carboxy-terminal extension can be expressed on lysozyme at high levels and without disrupting the stability of the fusion partner. Although the linker may consist of any sequence of amino acids, in order to reduce any adverse effects of the linker on the structural stability of the fusion protein, it is preferred that the linker has neutral structural properties, for example a neutral pH and small sized amino acids. A preferred carboxy terminal extension is flexible linker having the sequence (gly-gly-gly-gly-ser)$_3$ (SEQ ID NO 1). The provision of a fusion protein comprising a fusion partner protein and peptide joined by means of a flexible linker having the sequence (gly-gly-gly-gly-ser)$_3$ represents a third aspect of the present invention. Preferably, the fusion partner protein of the third aspect is lysozyme.

Apart from the presence of any carboxy-terminal linker sequence on the lysozyme fusion partner protein, there may be some variation in the sequence of the lysozyme from a natural sequence. Although natural, wild-type sequences of lysozyme are preferred, some variation from the natural sequence may be accommodated or, in some cases at least, desired, provided that the properties of lysozyme are not compromised to an unacceptable degree. Amino acid homology of at least 90% or 95% will be appropriate and generally not more than 2 or 3 amino acid changes will be preferred. Homology is determined by standard programs such as BLAST provided by the National Centre for Biotechnology Information (http://www.ncbi.nlm.nih.gov).

Lysozyme is basic in character. It has an isoelctric point of 10 to 11, and thus carries a positive charge up to this pH range. These characteristics have been exploited to purify lysozyme from other proteins, using techniques such as ion exchange chromatography and affinity chromatography. For example, cation exchange chromatography and affinity chromatography have been used in the purification of human saliva lysozyme (Vasstrad et al, (1980) *Scandinavian Journal of Dental Research* 88 219–228). Cation exchange chromatography has also been used in the purification of human airway lysozyme (Jacquet et al., (1987) *Analytical Biochemistry* 160: 227–232) and in the rapid purification of lysozyme from hen egg white (McCreath et al., (1997) *J. Chromatography A* 773: 73–83). The purification of lysozyme can also be accomplished using anion exchange chromatography in a negative mode. This technique has been used by in the purification of hen egg white lysozyme (Vachier and Awade (1995) *J. Chromatography B* 664: 201–210). In this case, hen egg white was diluted with a buffer at pH 9.0 and applied to a column of Q Sepharose FF (Amersham Pharmacia Biotechnology). At this pH most of the egg proteins had a net negative charge while the lysozyme still possessed a net positive charge and was either not retained or weakly bound to the column, thereby facilitating its purification. More sophisticated techniques for the purification of Lysozyme from a number of sources have also been described. For example, hydrophobic interaction chromatography following a cation exchange capture step has been used in the purification of lysozyme from horse milk, by exploiting a $Ca^{2+}$ dependant change in the hydrophobic/hydrophilic nature of Lysozyme which mediates its interaction with the hydrophobic resin (Noppe et al., *Journal of Chromatography A* 719: 327–331).

In the purification of bacteriophage lysozymes, two approaches have been taken. For the purification of phage lambda lysozyme expressed in *E. coli*, a negative purification step on an anion exchange resin (DEAE-cellulose) followed by a positive purification on a cation exchange resin (S-Sepharose Fast Flow, Amersham Pharmacia Biotechnology) was used (Jespers et al., (1991) *Protein Engineering* 4: 485–492). An alternative method whereby lysozyme is expressed with a poly-Histidine tag, thereby allowing its purification using immobilised metal ion affinity chromatography has also been used (During, (1993), *Protein Expression and Purification* 4: 412–416; Sloane et al., (1996) *J. of Biotechnology* 49: 231–238). This latter method for the purification of lysozyme requires the use of an affinity partner to aid its purification. It is surprising to note that the present invention is based upon the use of lysozyme as an ideal fusion partner to aid purification, whereas previous work discussed above suggests that lysozyme is a protein which itself requires an affinity partner for purification.

According to a preferred feature of the first aspect of the present invention, any suitable method may be used for purification of the fusion protein from the expression media. Preferably, a method for the purification of lysozyme will be used for initial and final purification. For example, precipitation techniques could be used. Lollike, K. et al., (Leukemia 9: 206–209, 1995) have described the purification of human lysozyme from neutrophils using a combination of PEG precipitation and column chromatography. The solubility characteristics of lysozyme have been studied in some depth (Curtis, R. A. et al., *Biotechnol. Bioeng.* 57: 11–21, 1998) and it has been recognised that solubility characteristics can be influenced by anion binding.

Precipitation with ammonium sulphate has also been used in the part purification of human milk proteins including Lysoszyme (Brignon, G & Ribadeau-Dumas, B., *Biochimie* 64: 231–235, 1982), again combined with chromatography; in this case, a size exclusion column. Size exclusion chromatography (SEC) may be considered a relatively high resolving technique for Lysozyme-peptide fusions due to their relatively small size. Following on from this, SEC could also be used as a way of separating the Lysozyme molecule from the peptide after cleavage. A new precipitation technique using carbon dioxide has also proved useful in the fractional precipitation of Lysozyme from protein mixtures (Winters, M. A. et al., *Biotechnol. Bioeng.* 62: 247–258. 1999), and may be applicable to the present invention.

Another technique which discriminates on the basis of size and that could be used for Lysozyme purification is filtration, in particular tangential flow filtration as disclosed in PCT WO 97/42835. Using this technique it may be possible to separate Lysozyme-peptides fusions or lysozyme from milk or other process fluids. It is further apparent that techniques such as either ion exchange chromatography or affinity exchange chromatography may be used. These methods are generally applicable and inexpensive, and can be used in the purification of lysozyme-peptide fusions from milk. In one such procedure, milk at a suitable pH and ionic strength could be applied to either a packed, fluidised or expanded bed for direct capture of the lysozyme fusion peptide. The majority of milk proteins being acidic in nature would be expected to pass through the column or to bind weakly to the resin, whereas the basic lysozyme fusion protein would bind tightly to the column. High purity material should result from elution with an increase in either ionic strength, solution conductivity, pH or a combination of any or all three. The use of a fluidised bed chromatography column for the purification of lysozyme from milk has been described recently in the literature (Noppe et al. *Journal of Chromatography A* 719: 327–331). Alternatively another procedure may be adopted by which a "negative" purification is used. In this application, milk is added to the anion exchanger using any of the column methods above whereby depending on the pH, acidic protein will become bound, whereas the lysozyme fusion protein would not bind or only bind weakly. If required, further purification of the lysozyme-peptide fusion protein may be carried out using either hydrophobic interaction chromatography or affinity chromatography, as discussed above.

It is therefore apparent that Lysozyme is a protein that lends itself to purification using a number of differing process operations thus increasing its attractiveness as a fusion partner. A general scheme for the purification of a lysozyme-peptide fusion may therefore be presented as a combination of low cost precipitation and/or filtration techniques optionally followed by the use of a number of column chromatographic techniques including, but not exclusively limited to, cation exchange chromatography, anion exchange chromatography, size exclusion chromatography and affinity chromatography. Although it would be of significant economic benefit if only low cost purification techniques, such as precipitation and filtration, are used, it may be expected that in most cases, the use of high resolution chromatographic techniques may be used to provide the high purity required for most pharmaceutical applications. Additionally, these chromatographic techniques would be useful in the elimination of possible pathogen such as viral particles. The applicability of any general purification scheme, once established, can than be validated for a number of different lysozyme fusions and, where necessary, changes in the unit operations or operating conditions can be made.

Once purified, the peptide can be released from the fusion protein by any suitable means. In order to achieve cleavage of the peptide, there is preferably provided a cleavage site between the fusion partner protein and peptide to enable release of the peptide from the fusion protein. Preferably, this is in addition to the flexible linker. Any suitable cleavage site may be used, including for example those which are cleaved by chemical or enzymatic means. An example of the former is treatment with cyanogen bromide which breaks peptide bonds at the carboxyl side of a methionine residue. The advantage of this method is that the reaction uses inexpensive reagents, but an important restriction is that there can be no internal methionine in the target peptide otherwise this too will be cut. However, methionine is a low abundance amino acid and many peptides of potential interest as commercial targets will satisfy this criterion. A second possible complication with cyanogen bromide may arise if the fusion partner also contains a methionine residue, since this could result in cleavage within the fusion partner, releasing a peptide which can interfere with the purification of the target peptide and adversely impact on production costs. This may be circumvented by using species of lysozyme which does not carry an internal methionine, for example human. Therefore, a fusion protein made from human lysozyme and salmon calcitonin, which also lacks an internal methionine, and preferably also a flexible linker would be a suitable candicate for cleavage by cyanogen bromide. In the case of salmon calcitonin, which has an amino cysteine residue, efficient cyanogen bromide cleavage requires the prior sulphonation of the adjacent thiol. This prevents an irreversible side reaction, and the thiol can be regenerated after the cleavage reaction is complete (Ray M. V. L et al (1993) *Bio/Technology* 11 64–70). A variety of other chemical cleavage reactions are also possible and any of these could be applied to the appropriately designed fusion protein (Han K. K et al., (1983) *Int. J. Biochem* 15 875–884).

A second preferred method of cleaving the fusion protein to release the peptide is to link the carboxy terminus of the fusion partner protein to the peptide via a sequence of amino acids which includes a specific recognition site for enzymatic cleavage, and which does not occur anywhere else in the fusion protein. Examples of such sites are the sequences Ile-Glu-Gly-Arg (SEQ ID NO. 2) and Asp-Asp-Asp-Lys (SEQ ID NO. 3), which are recognised and cleaved by blood factor Xa and enteorkinase respectively. This approach has the advantage that the cleavage enzyme can be chosen by reference to its recognition sequence; certain enzyme recognition sequences only occur very rarely in natural molecules, such as those quoted above. However, if at least part of the cleavage sequence occurs naturally at appropriate ends of the peptide or the fusion partner protein, then that fact can be used in the practice of the invention.

Where a linker is also present between the fusion partner protein and the peptide, in accordance with the second aspect of the invention, then the linker may be reduced or omitted as appropriate.

The cleavage site may contain more sequence than is absolutely necessary to direct cleavage. For example, in the case of a cleavage site recognised by enterokinase, the activation peptide of trypsinogen, the natural substitute cleaved by enterokinase, may be included as part of the linker. This has the sequence Phe-Pro-Thr-Asp-Asp-Asp-Lys (SEQ ID NO: 5).

It is important to note that the combination of the linker region, such as (gly-gly-gly-gly-ser)$_3$, (SEQ ID NO: 1) with either the cyanogen bromide cleavage site or the enterokinase cleavage recognition sequence still results in a high level expression of peptide. Part of this success in achieving high levels of peptide expression when using a fusion protein including a flexible linker in combination with a range of different cleavable sequences can be attributed to the neutral structural properties of the linker.

After cleavage, the peptide can be easily separated from the fusion partner protein by any convenient method. In the case of lysozyme, the efficient removal of the redundant fusion partner protein can be achieved by exploitation of the basic character of the protein, using for example ion exchange or affinity chromatography, as discussed above.

In the practice of the present invention, fusion proteins are produced in the milk of transgenic animals. The design and production of DNA sequences which encode the protein-peptide fusion proteins is well known to those skilled in the art (Sambrook et al., Molecular Cloning—A Laboratory manual, Cold Spring Harbor Laboratory Press, (2$^{nd}$ Edition) 1989). The lysozyme coding sequence can be obtained by screening libraries of genomic material or reverse translated messenger RNA derived from the animal of choice. These sequences are then cloned into an appropriate plasmid vector and amplified in a suitable host organism, usually *E. coli*. The DNA sequence encoding the peptide would then be constructed, for example by polymerase chain reaction amplification of a mixture of overlapping annealed oligonucleotides. If the production of a carboxy-terminal amino peptide was the objective then a glycine codon would also be introduced at the 3' terminus of the sequence encoding the peptide. This material would then be joined to the 3' end of the DNA encoding the lysozyme with the inclusion of a linker sequence, preferably according to the second aspect of the invention, including an appropriate fusion protein cleavage site. This entire construct after checking that the desired sequence has been constructed would be cloned into a suitable vector carrying control sequences suitable for the generation of transgenic animals.

After amplification of the vector, the DNA construct would be excised with the appropriate 3' and 5' control sequences, purified away from the remains of the vector and used to produce transgenic animals. Conversely, with some vectors, such as yeast artificial chromosomes (YACS), it is not necessary to remove the assembled vector; in such cases the vector may be used directly to make transgenic animals.

According to a fourth aspect of the present invention, there is provided an isolated or recombinant DNA molecule encoding a fusion protein, the DNA sequence comprising a coding sequence having a first segment encoding a fusion partner protein which is lysozyme coupled to a second segment encoding a peptide. Suitably, the coding sequence may be operatively linked to a control sequence, which enables the coding sequence to be expressed in the milk of a transgenic non-human placental animal.

To enable release of the peptide it is further desirable for the DNA molecule to include a sequence, provided between the first and second segments, which encodes a cleavage site, as discussed above in relation to the first aspect. Further, a flexible linker sequence may also be provided, with or without the cleavage site between the first and second segments. In a preferred feature, the linker has the sequence (gly-gly-gly-gly-ser)$_3$(SEQ ID NO: 1).

A DNA sequence which is suitable for directing the production to the milk of transgenic animals carries a 5' promoter region derived from a naturally derived milk protein and is consequently under the control of hormonal and tissue specific factors. Such a promoter is therefore most active in lactating mammary tissue. This promoter may be followed by a (usually shorter) DNA sequence directing the production of a protein leader sequence which would direct the secretion of the fusion protein across the epithelium into the milk. At the other end of the fusion protein construct a suitable 3' sequence, preferably also derived from a naturally occurring milk protein may be added. The 3' sequence performs various poorly defined functions and is to improve the stability of the transcribed RNA and thus increase the levels of the protein. An example of suitable control sequences for the production of proteins in the milk of transgenic animals are those derived from ovine β-lactoglobulin; see for example, WO-A-8800239 and WO-A-9005188, which describe these control sequences in particular, and more generally address the production of transgenic animals secreting proteins of interest in their milk.

The DNA molecules of the invention can conveniently form part of vectors, suitable for use in transforming host cells, either for the direct production of the fusion protein, or alternatively, for use in the production of a transgenic organism, preferably a non-human placental mammal, wherein the fusion protein is obtainable from the milk of said mammal. Suitable vectors include plasmids, such as those described herein, but other forms of vectors can be used and the skilled person will be aware of these and how they may be used/manipulated. Thus, such vectors form a sixth aspect of the invention. Host cells transformed with such vectors form a further aspect of the invention. Suitably, the host cells are mammalian.

Therefore, according to a yet further aspect of the present invention, there is provided a transgenic non-human placental mammal whose genome incorporates a DNA molecule comprising a coding sequence having a first segment encoding a fusion partner protein which is lysozyme coupled to a second segment encoding a peptide. The DNA molecule may also be modified as described above to incorporate such features as the control sequences, linker sequence and/or a cleavage site.

The production of transgenic animals can now be performed using a variety of methods. The most common of these is pronuclear injection where the DNA, having first been purified away from vector sequences, is directly injected into the male pronucleus. This can be done with either genomic sequences of cDNA constructs co-injected with genomic sequence for an endogenous milk protein (Clark, A. J et al (1992) Bio/Technology 10 1450–1454; and WO-A-9211358). Examples of other methods include cytoplasmic injection into ova, transformation of totipotent stem cells or carriage of foreign DNA sequences by sperm (Pursel, V. G and Rexroad, Jr C. E (1993) J. Anim. Sci 71 (Suppl. 3) 10–19). A wide variety of animals are suitable for transgenic expression in milk, including cows, sheep, goats, rabbits, mice and pigs. Essentially, any species which is domesticated and produces sufficient quantities of harvestable milk would be preferable for the production of lysozyme-peptide fusion proteins.

In a final aspect of the present invention, there is provided a composition comprising a fusion protein of the invention. The composition may be expression media derived from a transgenic, non-human placental animal, and preferably is milk.

Preferred features of each aspect of the present invention are as for each other aspect, mutatis mutandis.

BRIEF DESCRIPTION OF THE DRAWINGS

The invention will now be illustrated by the following Examples, with reference to the figures, in which:

FIG. 2A-D show the DNA sequence of pCLYSM, excluding the bacterial plasmid (SEQ ID NO. 4).

FIG. 3 shows the results of mass analysis of pCLYSM fusion purified from mouse milk.

Criteria Used In Hypermass Calculation:
Agent: , Mass: 1.0079, Charge: 1, Agent Gained
Charge Estimation Tolerance: 0.1000
Tolerance Between Mass Estimates: 20.0000

| Peak | Intensity | Predicted Peak | Charge | Hypermass Estimate |
|---|---|---|---|---|
| 1404.13 | 94062.50 | 1404.13 | 14.00000 | 19643.73 |
| 1512.03 | 61250.00 | 1511.62 | 13.00353 | 19643.35 |
| 1637.84 | 33750.00 | 1636.35 | 12.01093 | 19641.98 |
| 1786.54 | 28750.00 | 1785.37 | 11.00723 | 19640.90 |

Final Estimated Mass: 19642.49
Standard Deviation: 1.30

Figure 4:
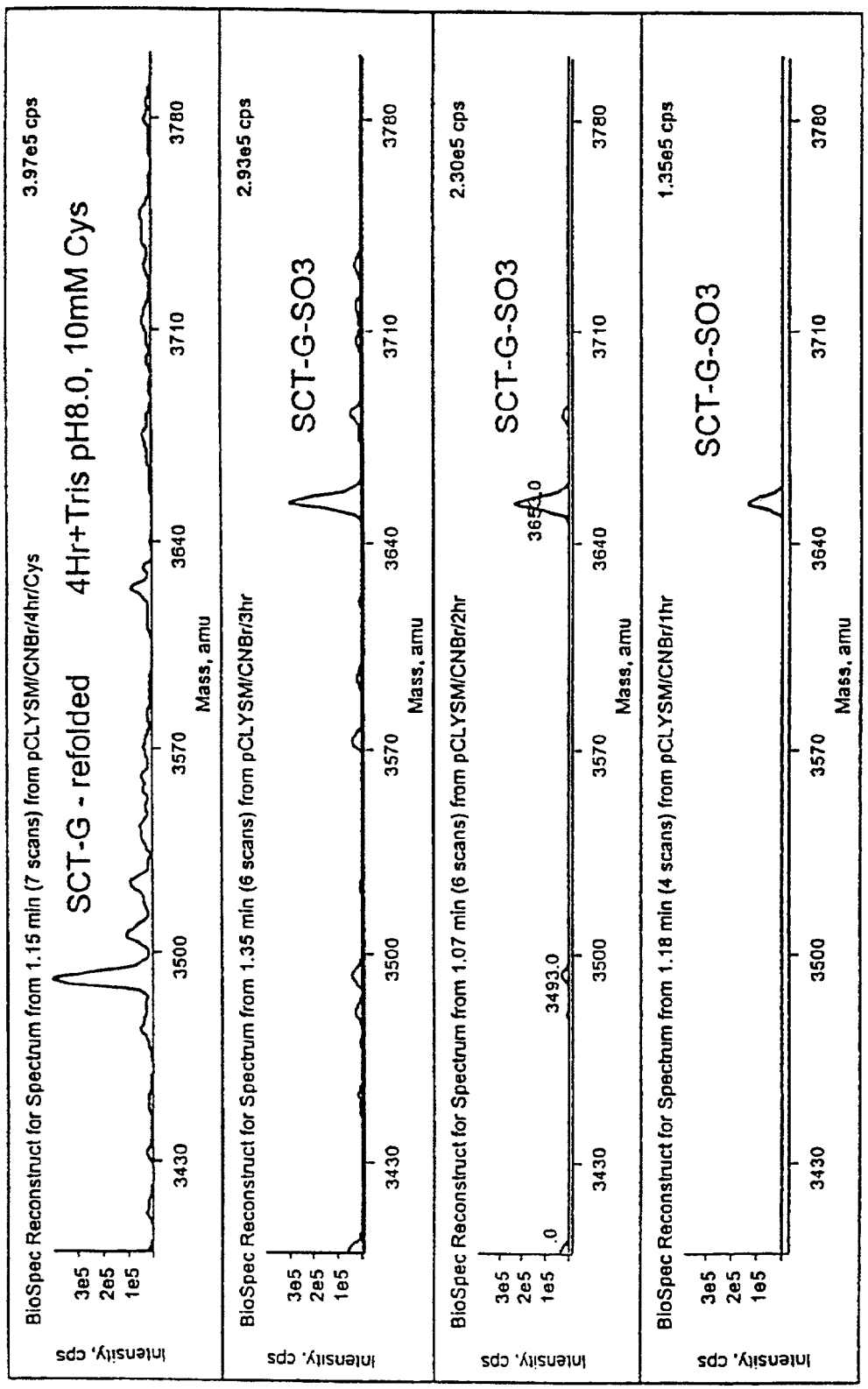

FIG. 4 shows the monitoring of cyanogen Bromide cleavage and sCT re-folding by mass analysis.

Figure 5:
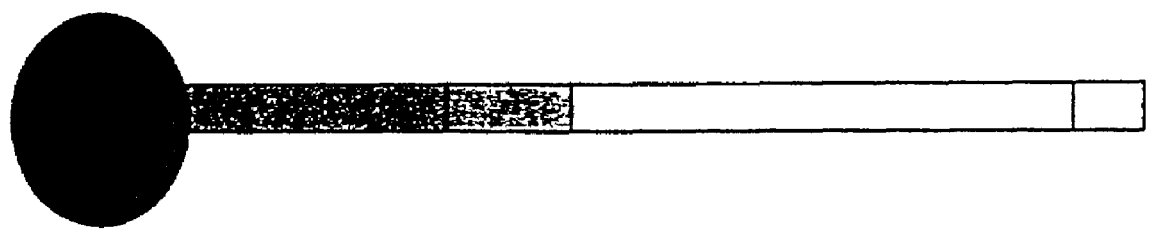

FIG. 5 is a diagrammatic illustration of the lysozyme-linker-enetrokinase-GLP-1 fusion construct.

| Species | Predicted Mass |
|---|---|
| Fusion-Gly | 19968 Da |
| Fusion amidated | 19911 Da |
| GLP-1 7–37 | 3355 Da |
| GLP-1 7–36 amide | 3298 Da |

Figure 6:
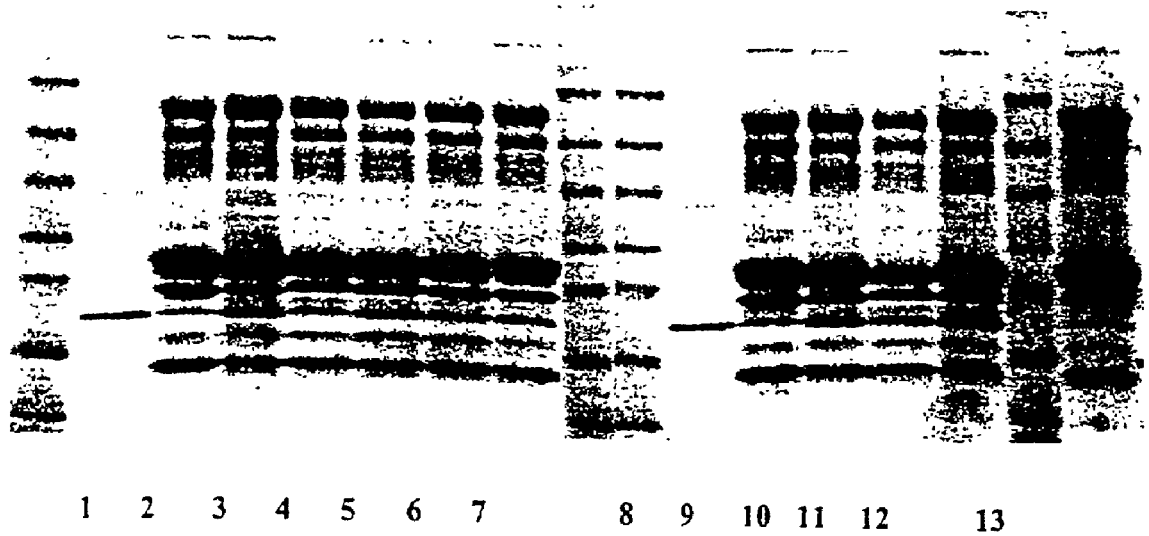

FIG. 6 shows SDS-PAGE analysis of GLP-1 fusion milks.
Lanes 1 and 8 Partially purified GLP-1 Fusion
Lanes 2 and 9 Control rabbit milk

| Lane 3 | GLP-1 Line 2 | Lane 10 | GLP-1 Line 50 |
| Lane 4 | GLP-1 Line 20 | Lane 11 | GLP-1 Line 61 |
| Lane 5 | GLP-1 Line 21 | Lane 12 | GLP-1 Line 64 |
| Lane 6 | GLP-1 Line 38 | Lane 13 | GLP-1 Line 66 |
| Lane 7 | GLP-1 Line 46 | | |

Figure 7:

FIG. 7 shows a western blot analysis of selected GLP-1 fusion milks.

| Lanes 1 and 6 | Control Rabbit Milk |
| Lanes 2 and 7 | GLP Line 2 |
| Lanes 3 and 8 | GLP Line 21 |
| Lanes 4 and 9 | GLP Line 50 |
| Lanes 5 and 10 | GLP Line 64 |

FIG. 8 shows ESI-MS analysis of GLP-1 fusion milks.

Figure 9:
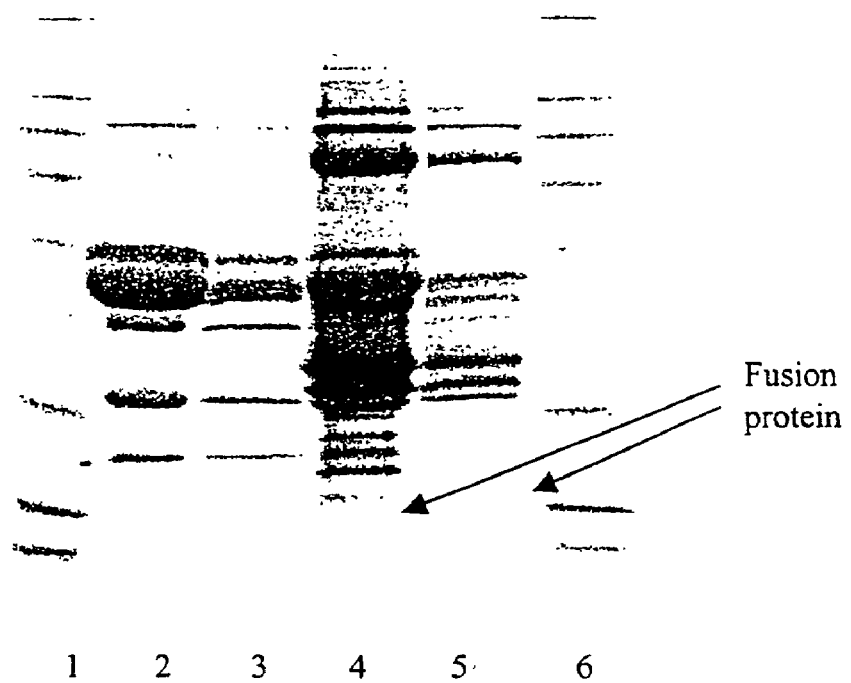

FIG. 9 shows an 8DS-PAGE gel (Coomassie blue stained) of milk obtained from the sheep expressing the lysozyme—enterokinase clearable linker—calcitonin fusion protein, as discussed in Example 3.

Figure 10:
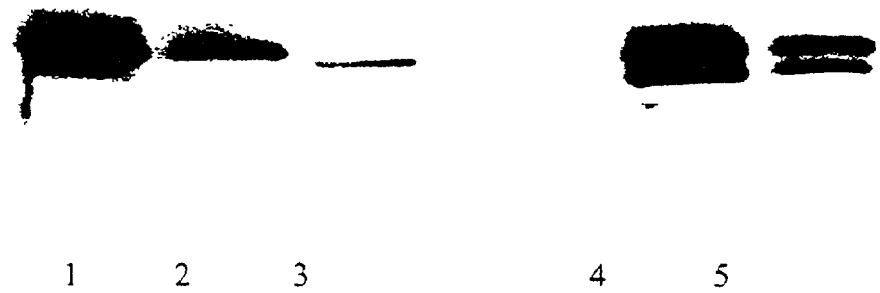

FIG. 10 shows a Western blot of the fusion protein of Example 3 after a single cation exchange purification step.

EXAMPLES

Example 1

A Comparison of Expression Levels in Mice Using α-Lactalbumin and Lysozyme Fusion Proteins Both Joined to Calcitonin Via a Cyanogen Bromide Cleavable Linker Two constructs were designed to express calcitonin fusion proteins. The first termed pCALM, was designed to express a human alpha-lactalbumin/salmon calcitonin fusion protein in the milk of transgenic animals. This fusion protein allows the release of calcitonin from the end of a linker arm fused to the alpha-lactalbumin C terminal by cyanogen bromide (CNBr) chemical cleavage.

pCALM Structure pCALM consists of:
1. A 4.2 kb region comprising the ovine b-lactoglobin (BLG) promoter and 5' untranslated region (UTR).
2. A 2069 bp region comprising the complete coding region of the human alpha lactalbumin gene corresponding to bases 750 to 2819 of the human alpha lactalbumin sequence (EMBL+Genbank database, accession number: X05153), previously derived from a library of cloned human genomic DNA in bacteriophage lambda.
3. A 162 bp region encoding a C terminal extension to the alpha-lactalbumin protein, comprising a $(Gly_4 Ser)_3$ Ala Ser linker arm (SEQ ID NO: 6), CnBr cleavage site and salmon calcitonin peptide sequence extended by a single Gly residue to facilitate C-terminal amidation and translational stop signal.
4. A 2.5 kb region comprising the 3' UTR, polyadenylation site and 3' flanking region of the ovine beta-lactoglobulin gene.
5. A 242 bp region comprising the chick b-globin insulator region (U.S. Pat. No. 5,610,053).
6. The pUC18 bacterial plasmid vector.

Further details about some of the components of pCALM are described in McKee C, et al., *Nat Biotechnol* 1998 July; 16(7):647–51

A second construct, termed pCLYSM, was designed to express a human lysozyme—salmon calcitonin fusion protein in the milk of transgenic animals. This fusion protein allows the release of calcitonin from the end of a linker arm fused to the lysozyme C terminal by cyanogen bromide chemical cleavage.

pCLYSM Structure

Figure 1:
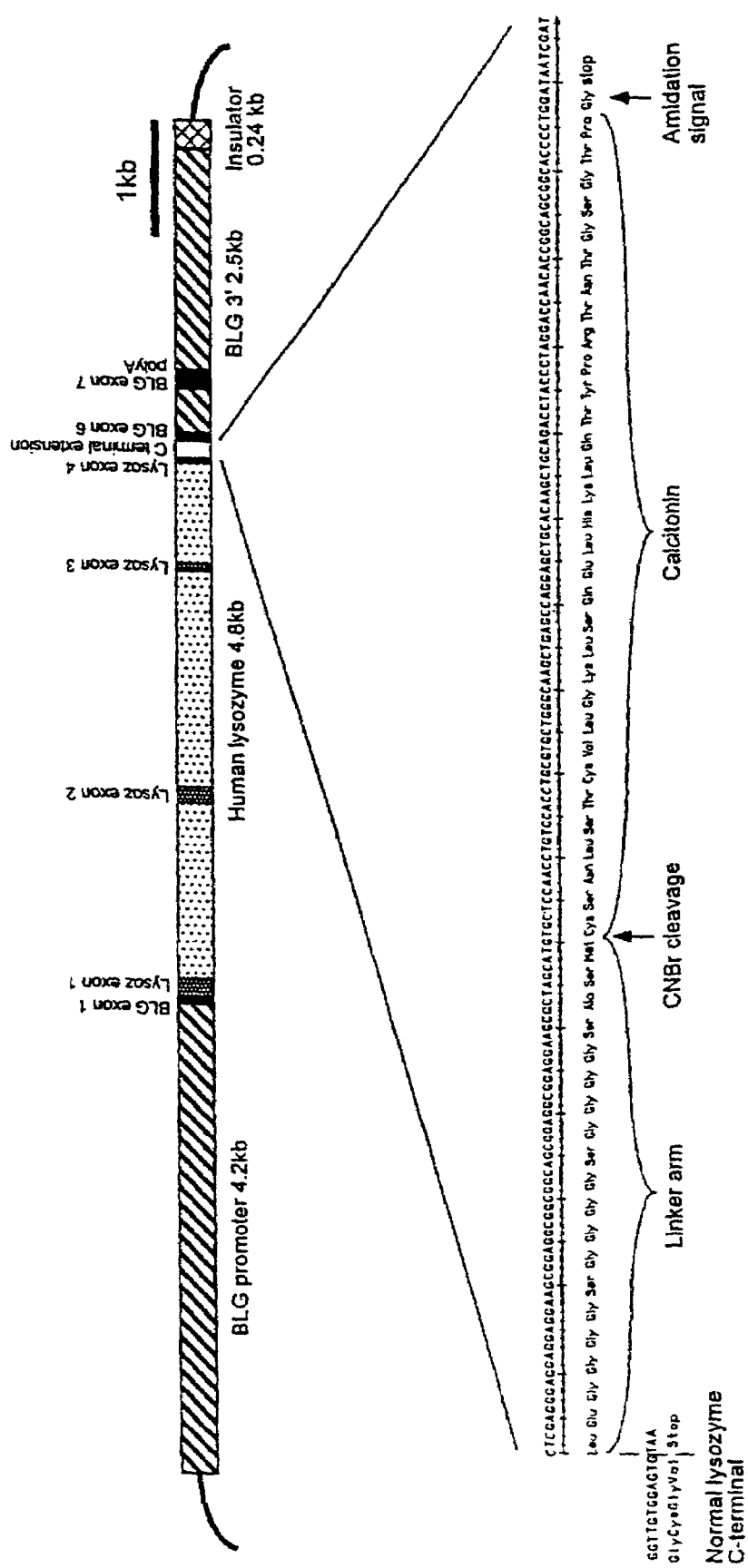
FIG. 1 shows the structure of pCLYSM construct (Normal lysozyme C-terminal DNA and amino acid sequence. SEQ ID NO.: 8; C-terminal amino acid sequence alone SEQ ID NO.: 9; Linker arm, CNBr cleavage, Calcitonin and Amidation signal DNA and amino acid sequence. SEQ ID NO.: 10).

The structure of pCLYSM is shown in FIG. 1, and the sequence in FIG. 2A–D.

pCLYSM consists of:
1. A 4.2 kb region comprising the ovine β-lactoglobin (BLG) promoter and 5' untranslated region (UTR).
2. A 4.8 kb region comprising the complete coding region of the human lysozyme gene corresponding to bases 520 to 5345 of the human lysozyme sequence (EMBL+Genbank database, accession number: X14008), derived by polymerase chain reaction (PCR) amplification of genomic DNA prepared from the human cell line HT1080.
3. A 162 bp region encoding a C terminal extension to the lysozyme protein, comprising a $(Gly_4 Ser)_3$ Ala Ser linker arm (SEQ ID NO: 6), CNBr cleavage site and salmon calcitonin peptide sequence extended by a single Gly residue to facilitate C-terminal amidation.
4. A 2.5 kb region comprising the 3' UTR, polyadenylation site and 3' flanking region of the ovine BLG gene.
5. A 242 bp region comprising the chick α-globin insulator region (U.S. Pat. No. 5,610,053)
6. The pUC18 bacterial plasmid vector.

Although the insulator region was included in this construct it was not essential to the production of the fusion protein.

Expression of pCALM and pCLYSM in Transgenic Mice pCALM and pCLYSM were introduced into mouse zygotes by pronuclear microinjection using standard procedures (Palmiter et al., (1982) *Nature* 300: 611–615). Mice containing the pCALM or the pCLYSM transgenes were identified by PCR analysis and Southern blotting. Milk was obtained from these mice and analyzed by a combination of SDS-PAGE, western blotting and RID.

Copy Numbers and Expression Data for pCALM Mouse Lines.

| Line | Copy No. | Expression Level mg/ml |
| --- | --- | --- |
| 1.40 | 20 | 0.26 |
| 1.7 | 30 | 0.13 |
| 2.22 | 20 | 0.13 |
| 3.18 | 2 | 0.26 |
| 3.27 | 2 | 0.13 |
| 3.38 | 1 | 0.026 |
| 3.4 | 1 | 0.026 |
| 5.1 | 7 | 0.26 |
| 5.7 | 10 | 0.26 |
| 6.1 | 7 | 0.26 |
| 7.1 | 1 | 0.013 |
| 8.18 | 3 | 0.13 |

Copy Numbers and Expression Levels of pCLYSM Mouse Lines

| Line | Copy No. | Expression Level mg/ml |
| --- | --- | --- |
| 156.6 | 10 | 9.8 |
| 156.6.1 | >30 | 5.4 |
| 156.6.2 | >30 | 11 |
| 156.6.3 | 10–30 | 9.8 |
| 159.11 | 1 | 0.55 |
| 159.3 | 10 | 0.13 |
| 161.17 | 10 | 2.75 |
| 161.2 | 1 | 1 |
| 162.10 | 5 | 4.74 |
| 162.13 | 1 | 1.20 |
| 162.15 | 1 | 0.4 |
| 162.8 | 5 | 6.4 |
| 162.8.1 | 1 | 5.4 |
| 162.8.2 | 1 | 7.5 |
| 162.8.3 | 1 | 7.5 |
| 163.13 | 30 | 2.23 |
| 163.3 | 20 | 5 |
| 164.18 | 2 | 1.09 |

Characterisation of the Lysozyme Fusion Protein.

In view of the high expression levels of the lysozyme fusion protein it is possible to purify sufficient material from mouse milk for further characterisation and cyanogen bromide cleavage. The pCLYSM protein product was purified from EDTA solubilized milk by cation exchange chromatography and further characterized by mass analysis. The observed mass of 19642.5 Da is consistent with the full length fusion protein containing five disulphide bridges, four in lysozyme and one in sCT (FIG. 3).

Prior to CNBr cleavage the cysteine residues were sulphonated according to the method of Ray et al (Biotechnology Vol. 11 January 1993). Briefly, the fusion protein was incubated at pH 8.0 in the dark for 12 hrs with a 10 fold molar excess of sodium sulphite and a 2 fold molar excess of sodium tetrathionate. Following desalting, the sulphonated protein was cleaved in 8M urea, 50 mM HCl pH 8.0 containing 1 mg CNBr/mg protein. Cleavage was monitored by mass analysis and final refolding of sCT achieved by 10 fold dilution of the reaction mixture into 0.1M Tris/Cl pH 8.0, 10 mM cysteine (FIG. 4)

Example 2

Production of a Human Lysozyme—Glucagon-Like Peptide 1 (GLP-1) in the Milk of Transgenic Rabbits Details of the GLP-1 construct:

A construct termed pGLUC-1 was designed to express a human lysozyme/human glucagon-like peptide 1 GLP1 fusion protein in the milk of transgenic animals. This fusion protein allows the release of GLP1 from the end of a linker arm fused to the lysozyme C terminal by enterokinase enzymic cleavage.

pGLUC1 Structure

The structure of pGLUC1 is identical to pCLYSM, as described in example 1, apart from the C terminal extension to the lysozyme protein. pGLUC1 consists of:
1. A 4.2 kb region comprising the ovine b-lactoglobin (BLG) promoter and 5' untranslated region (UTR).
2. A 4.8 kb region comprising the complete coding region of the human lysozyme gene corresponding to bases 519 to 5344 of the human lysozyme sequence (EMBL+Genbank database, accession number: X14008), derived by polymerase chain reaction (PCR) amplification of genomic DNA prepared from the human cell line HT1080.
3. A 162 bp region encoding a C terminal extension to the lysozyme protein, comprising a [(Gly$_4$ Ser)$_3$ Ala Ser] linker arm (SEQ ID NO: 6), a (Asp Asp Asp Asp Lys) enterokinase cleavage site (SEQ ID NO: 3), a 30 amino acid region corresponding to residues 7–36 of the human GLP1 sequence followed by a single Gly residue to facilitate C-terminal amidation and a translational stop signal.
4. A 2.5 kb region comprising the 3' UTR, polyadenylation site and 3' flanking region of the ovine BLG gene.
5. A 242 bp region comprising the chick b-globin insulator region (U.S. Pat. No. 5,610,053)
6. The pUC18 bacterial plasmid vector.

A construct coding for human lysozyme, a flexible enterokinase cleavable linker and GLP 7-37 was microinjected into the nucleus of recently fertilised rabbit embryos. The last glycine residue of the peptide was expected to act as a suitable substrate for the amidating enzyme, PAM. The embryos were transplanted into recipient does and the resultant kits screened for the transgene by PCR and Southern analysis. A total of 12 transgenic offspring were produced (3 females and 9 males). All offspring were induced to lactate with oxytocin injections, the females at two months and the males at three. Milk samples were collected for five days or until the rabbits dried off, which ever was the shorter.

2. Milk Analysis 2.1 Human Lysozyme Radial Immuno Diffusion Analysis

All milks were analysed on Human Lysozyme RID plates obtained from the Binding site. Control rabbit milk produced no signal at 1 in 100 dilution (in assay diluent supplied with the kit) whereas the transgenic milks produced precipitin rings from 1 in 250 to 1 in 4000. The expression levels by RID are as follows:

| Rabbit No. | Sex | Milk Volume (mls) | Expression (mg/ml) |
|---|---|---|---|
| 2 | M | 10.75 | 17.7 |
| 20 | M | 8 | 0.9 |
| 21 | M | 20.7 | 16.6 |
| 38 | M | 31.75 | 3.75 |
| 46 | M | 13.5 | 4.47 |
| 50 | M | 4.35 | 17.5 |
| 60 | F | Drops | >40 |
| 61 | F | 13.9 | 14.6 |
| 64 | M | 1.3 | 31.0 |
| 66 | F | 0.25 | 3.05 |

RID values were measured against human lysozyme, assuming that GLP-1 fusion and lysozyme have the same response. To validate this the Coomassie Blue staining intensity for GLP-1 milks and lysozyme standards were compared—the RID and Coomassie Blue estimates were in broad agreement.

2.2 SDS-PAGE

Milk from each founder and a non-transgenic control rabbit was diluted in reducing Laemmli buffer and run at the equivalent of 0.1 µl on a 4–20% Novex gel. The gel was visualised with Coomassie Blue stain (FIG. 6). Although rabbit milk has a band that co-migrates with the GLP-1 fusion, it is clear that the high expressing milks have a much more intense band in this position. Rabbit 60 is not included because it is deemed to be a failed induction and not representative of a natural lactation.

2.3 Amino-Terminal Sequence Analysis

In order to confirm the identity of the over-expressed protein N-terminal sequence analysis was carried out. 1 µl of milk from Male No. 2 was run on a 4–20% Novex gel as described above and electroblotted to PVDF membrane. The membrane was stained briefly with Coomassie Blue and the fusion band cut out for Edman sequencing. A strong sequence corresponding to that of human lysozyme was observed. The co-migrating band was not identified, although it is presumably a rabbit casein which is not in the Swiss Prot database.

2.4 Western Blotting for Human Lysozyme and GLP-1

In order to further confirm the identity of the fusion protein Western blotting was done with both anti lysozyme and anti GLP-1 antibodies. Four high expressing milks (2, 21, 50 and 64) and control rabbit milk were run in duplicate at 0.01 µl on 4–20% Novex gels and transferred to PVDF membrane for western blotting. Membranes were blocked with 2% BSA in PBS, 0.1% Tween 20 and then probed with Dako Rabbit anti human lysozyme or GLP-1 Mab. The blots were visualised with ECL reagent from Pierce and Amersham Hyperfilm. While control rabbit milk gave no signal, a single band which cross-reacts with both antibodies was observed in each transgenic milk (FIG. 7). Milk 64 alone gave rise to two minor bands, one above and one below the main signal—the identity of these species is not yet known.

2.5 GLP Fusion Purification Purification

Lysozyme was chosen as a fusion partner because of its basicity and resultant ease of purification from the main acidic proteins in milk by cation exchange chromatography. GLP-1 milks were mixed with an equal volume of 200 mM EDTA pH 8.0 (to dissociate the casein micelles) and then diluted 10 fold in 20 mM Tris/Cl pH 7.0. This feedstock was bound on a Pharmacia Mono S column equilibrated in the same buffer and eluted with a gradient of 0–0.5M NaCl. A single peak containing GLP-1 fusion and associated caseins eluted early in the gradient. Although not pure this material was suitable for analysis by Electro Spray Ionisation-Mass Spectroscopy (ESI-MS).

2.6.ESI-MS Analysis and Enterokinase Cleavage

ESI-MS analysis was performed using a API100 mass spectrometer (Perkin Elmer). Samples were applied using Micro Protein Cartridges, 1.0×10 mm C8, washed with 0.1% acetic acid and eluted with 0.1% acetic acid in acetonitrile. Mass calibration was performed using Polyproyleneglycol standards.

Mass analysis revealed two species, the major one being consistent with amidated GLP-1 fusion with conversion of the C-terminal Gly to Arg-amide, the second minor species 80 Da higher (FIG. 8). Treatment of the fusion with alkaline phosphatase confirmed that the 80 Da increase was due to phosphorylation, a modification found in other milk proteins. Incubation of the fusion with enterokinase followed by mass analysis revealed that the phosphate group was on the fusion partner not GLP-1 and confirmed the release of fully amidated peptide (FIG. 8). The analysis described above was applied to lines 2, 20, 21, 38, 61 and 66. All showed the same pattern of phosphorylation and were also fully amidated.

3. Summary

A total of 10 transgenic founders for the GLP-1 fusion were produced. All lines were found to express the fusion protein as judged by human lysozyme RID, SDS-PAGE and western blotting analysis at between 0.9 and 31 mg/ml. The fusion was easily purified by cation exchange chromatography, allowing characterisation by ESI-MS and cleavage with enterokinase to yield GLP-1 7–36amide. Processing of the glycine extension by endogenous PAM activity was very efficient and no residual glycine extended fusion was detected.

Example 3

Analysis of the Expression in Sheep of a Lysozyme Fusion Protein Joined to Calcitonin Via an Enterokinase Cleavable Linker A construct, designated CALC11, was designed for the expression of a calcitonin fusion protein in the milk of transgenic sheep. This fusion protein allows the release of calcitonin from the end of the linker arm fused to lysozyme by incubation with the protease enterokinase.

The structure of the CALC11 construct is identical to that described for pCLYSM except that the CNBr cleavage site (methionine) is replaced by an enterokinase cleavage site (aspartic acid-aspartic acid-aspartic acid-aspartic acid-lysine)(SEQ ID NO: 3).

A CALC11 transgenic sheep was generated by nuclear transfer as described in WO 97/07669 and WO 97/07668. Milk obtained from induced lactation of this animal was analysed by a combination of SDS-PAGE and Western blotting.

FIG. 9 shows an SDS-PAGE gel (Coomassie Blue stained) of milk obtained from the sheep expressing the lysozyme-enterokinase cleavable linker-calcitonin fusion protein.

Lanes 1 and 6—molecular weight markers

Lanes 2 and 3—Control sheep milk

Lanes 4 and 5—lysozyme-calcitonin fusion milk

The fusion protein is clearly visible in transgenic milk (arrows), compared to control milk. The second new band, below the fusion protein, is a clipped fusion protein where part of the carboxy terminus has been removed during the secretory process by an unidentified protease.

The level of expression of the lysozyme-enterokinase cleavable linker-calcitonin fusion protein in the sheep milk, based on a gel comparison of the purified fusion protein and a known quantity of lysozyme, is 5 mg/ml.

FIG. 10 shows a Western blot of the fusion protein after a single cation exchange purification step.

Lanes 1, 2—purified lysozyme-enterokinase cleavable linker-calcitonin fusion protein probed with anti-calcitonin antibody Lane 3—purified α-lactalbumin-calcitonin fusion protein probed with anti-calcitonin antibody (used as a control to show specificity of the calcitonin antibody). The production and characterisation of this fusion protein is described elsewhere (McKee C. et al (1998) *Nat. Biotechnol.* 16(7) 647–651).

Lanes 4 and 5 purified lysozyme-enterokinase cleavable linker-calcitonin fusion protein probed with anti-lysozyme antibody.

Probing with the antibody to calcitonin confirms the presence of the calcitonin peptide as part of the fusion protein and shows that, as expected, the size of the lysozyme fusion is similar to that of the α lactalbumin calcitonin fusion used as a standard. The presence of the lysozyme component of the fusion protein is also confirmed by blotting with the antibody to lysozyme. Note the absence of the lower band of the doublet as probed with the antibody to calcitonin confirming that the second band on the SDS-Page gel shown above is indeed truncated before the peptide portion. However, this clipped version is a minor component and does not detract from the observation that full size lysozyme calcitonin fusion has been expressed at a high level in the milk of a transgenic sheep.

What is claimed is:

1. A transgenic non-human placental mammal whose genome incorporates a DNA molecule comprising a coding sequence operably linked to a control sequence which comprises a promoter from a gene encoding a naturally-derived milk protein, wherein said coding sequence comprises in order a first segment encoding a fusion partner protein which is lysozyme coupled in-frame to a second segment encoding a peptide other than a protein leader sequence and wherein said fusion protein is expressed in the milk of said transgenic animal.

2. A transgenic mammal as claimed in claim 1, wherein said mammal is selected from the group consisting of a cow, a sheep, a goat, a rabbit, a mouse and a pig.

3. The transgenic animal of claim 1, wherein said promoter sequence is a β-lactoglobulin promoter.

4. The transgenic animal of claim 1, wherein said second segment encodes a peptide selected from the group consisting of:
   (a) calcitonin;
   (b) parathyroid hormone;
   (c) glucagon;
   (d) glucagon-like-peptide-1;
   (e) a magainin;
   (f) a histatin;
   (g) a protegrin; and
   (h) a clavanin.

5. The transgenic animal of claim 1, wherein said lysozyme is human lysozyme.

* * * * *

SEQUENCE LISTING

<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Linker

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Recognition
      site for enzymatic cleavage

<400> SEQUENCE: 2

Ile Glu Gly Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Recognition
      site for enzymatic cleavage

<400> SEQUENCE: 3

Asp Asp Asp Lys
1

<210> SEQ ID NO 4
<211> LENGTH: 12061
<212> TYPE: DNA
<213> ORGANISM: Artificial Sequence
<220> FEATURE:
<223> OTHER INFORMATION: Description of Artificial Sequence: DNA
      sequence of pCLYSM, excluding the bacterial plasmid

<400> SEQUENCE: 4

| | | | | | |
|---|---|---|---|---|---|
| aagcttgcat | gcctgcaggt | cgacctgcag | gtcaacggat | ctctgtgtct | gttttcatgt | 60 |
| tagtaccaca | ctgttttggt | ggctgtagct | ttcagctaca | gtctgaagtc | ataaagcctg | 120 |
| gtacctccag | ctctgttctc | tctcaagatt | gtgttctgct | gtttgggtct | ttagtgtctc | 180 |
| cacacaattt | ttagaattgt | ttgttctagt | tctgtgaaaa | atgatgctgg | tattttgata | 240 |
| aggattgcat | tgaatctgta | aagctacaga | tatagtcatt | gggtagtaca | gtcactttaa | 300 |
| caatattaac | tcttcacatc | tgtgagcatg | atatattttc | ccctctata | tcatcttcaa | 360 |
| ttcctcctat | cagtttcttt | cattgcagtt | ttctgagtac | aggtcttaca | cctccttggt | 420 |
| tagagtcatt | cctcagtatt | ttattccttt | gatacaattg | tgaatgaggt | aattttctta | 480 |
| gtttctcttt | ctgatagctc | attgttagtg | tatatataga | aaagcaacag | atttctatgt | 540 |
| attaattttg | tatcctgcaa | cagatttcta | tgtattaatt | ttgtatcctg | ctactttacg | 600 |
| gaattcactt | attagctttt | tggtgacatc | ttgaggattt | tctgaagaaa | atggcatggt | 660 |
| atggtaggac | aaggtgtcat | gtcatctgca | aacagtggca | gttttccttc | ttcccttcca | 720 |
| acctggatttt | ctttgatttc | tttctgtctg | agtacgacta | ggattcccaa | tactataccg | 780 |
| aataaaagtg | gcaagagtgg | acatccttgt | cttatttttc | tgaccttaga | ggaaatgctt | 840 |
| tcagttttttc | accattaatt | ataatgttta | ctgtgggctt | gtcatatgtg | gccttcatta | 900 |
| tatggaggtc | tattccctct | atacccacct | tgttgagagt | ttttatcata | aaagtatgtt | 960 |
| gaattttgtc | aaaagttttt | cctgcatcta | ttgagatgat | ttttactctt | caattcatta | 1020 |

-continued

```
atgatttta ttcttcattt tgttaatgat ttccattctt caatttgtta acgtggtata      1080
tcacattgat tgatttgtgg atacctttgt atccctggga taaacctcac ttgatcatga      1140
gctttcaatg tatttttgaa ttcactttgc taatattctg ttgggtattt ttgcatctct      1200
attcatcaat gatattggcc taagaaaggt tttgtctggt tttagtatca gggtgatgct      1260
ggcctcatag agagagttta gaagcatttc ctcctctttg attttcgga atagtttgag       1320 taggataggt attaactctt ctttaaatgt ttggggactt ccctggtgag ccggtggttg      1380
agaatccgcc tcaggatgt gggtttgatc cctggtcagg gaaccattaa taagatccca       1440
catgctgcag ggcaacaagc ccccaagctg caaccactga gctgcaaccg ctgcagtgcc      1500
cacaggccac gaccagagaa agcccacata cagcagggaa gacccagcac aaccggaaaa      1560
aggagtttgg tggaatacag ctgtgaagcc gtctggtcct ggactcctgc ttgagggaat      1620 ttttaaaaa ttattgattc aatttcatta ctggtaactg gtctgttcat attttctatt       1680
tcttccgggt tcagtcttgg gagattgtac atgcctagga atgtgtccgt ttcttctagg      1740
ttgtccattt tattggacat gcatgggagc acacagcacc gaccagcgag actcatgctg      1800
gcttcctggg gccagggctg gggccccaag cagcatggca tcctagagtg tgtgaaagcc      1860
cactgaccct gcccagcccc acaatttcat tctgagaagt gattccttgc ttctgcactt      1920
acaggcccag gatctgacct gcttctgagg agcaggggtt ttggcaggac ggggagatgc      1980
tgagagccga cggggtccca ggtcccctcc caggcccccc tgtctggggc agcccttggg      2040
aaagattgcc ccagtctccc tcctacagtg gtcagtccca gctgcccag gccagagctg       2100 ctttatttcc gtctctctct ctggatggta ttctctggaa gctgaaggtt cctggaagtt      2160
atgaatagct ttgccctgaa gggcatggtt tgtggtcacg gttcacagga acttgggaga      2220
ccctgcagct cagacgtccc gagattggtg gcacccagat ttcctaagct cgctggggaa      2280
cagggcgctt gtttctccct ggctgacctc cctcctccct gcatcaccca gttctgaaag      2340
cagagcggtg ctgggtcac agcctctcgc atctaacgcc ggtgtccaaa ccaccgtgc        2400 tggtgttcgg ggggctacct atggggaagg gcttctcact gcagtggtgc cccccgtccc     2460
ctctgagatc agaagtccca gtccggacgt caaacaggcc gagctccctc cagaggctcc      2520
agggagggat ccttgccccc ccgctgctgc ctccagctcc tggtgccgca ccctttgagcc     2580 tgatcttgta gacgcctcag tctagtctct gcctccgtgt tcacacgcct ctccccatg      2640 tccctccgt gtccccgttt tctctcacaa ggacaccgga cattagatta gcccctgttc       2700
cagcctcacc tgaacagctc acatctgtaa agacctagat tccaaacaag attccaacct     2760
gaagttcccg gtggatgtga gttctggggc gacatccttc aaccccatca cagcttgcag      2820
ttcatcgcaa aacatggaac ctgggggttta tcgtaaaacc caggttcttc atgaaacact     2880
gagcttcgag gcttgttgca agaattaaag gtgctaatac agatcagggc aaggactgaa     2940
gctggctaag cctcctcttt ccatcacagg aaaggggggc ctgggggcgg ctggaggtct     3000
gctcccgtga gtgagctctt tcctgctaca gtcaccaaca gtctctctgg gaaggaaacc     3060
agaggccaga gagcaagccg gagctagttt aggagacccc tgaacctcca cccaagatgc     3120
tgaccaggcc agcgggcccc ctggaaagac cctacagttc agggggggaag agggggctgac    3180 ccgccaggtc cctgctatca ggagacatcc ccgctatcag gagattcccc caccttgctc     3240
ccgttcccct atcccaatac gcccacccca ccctgtgat gagcagttta gtcacttaga      3300
atgtcaactg aaggcttttg catcccctt gccagaggca caaggcaccc acagcctgct      3360
gggtaccgac gcccatgtgg attcagccag gaggcctgtc ctgcaccctc cctgctcggg     3420
```

```
ccccctctgt gctcagcaac acacccagca ccagcattcc cgctgctcct gaggtctgca   3480
ggcagctcgc tgtagcctga gcggtgtgga gggaagtgtc ctgggagatt aaaatgtga    3540 gaggcgggag gtgggaggtt gggccctgtg gcctgccca tcccacgtgc ctgcattagc    3600
cccagtgctg ctcagccgtg cccccgccgc agggtcagg tcactttccc gtcctggggt    3660
tattatgact cttgtcattg ccattgccat ttttgctacc ctaactgggc agcaggtgct   3720
tgcagagccc tcgataccga ccaggtcctc cctcggagct cgacctgaac cccatgtcac   3780
ccttgcccca gcctgcagag ggtgggtgac tgcagagatc ccttcaccca aggccacggt   3840
cacatggttt ggaggagctg gtgcccaagg cagaggccac cctccaggac acacctgtcc   3900
ccagtgctgg ctctgacctg tccttgtcta agaggctgac cccggaagtg ttcctggcac   3960
tggcagccag cctggaccca gagtccagac acccacctgt gcccccgctt ctgggtcta   4020 ccaggaaccg tctaggccca gaggggact tcctgcttgg ccttggatgg aagaaggcct   4080
cctattgtcc tcgtagagga agccaccccg gggcctgagg atgagccaag tgggattccg   4140
ggaaccgcgt ggctggggc ccagcccggg ctggctggcc tgcatgcctc ctgtataagg    4200
ccccaagcct gctgtctcag ccctccactc cctgcagagc tcagaagcac gaccccaggg   4260
atcctgccta gcactctgac ctagcagtca acatgaaggc tctcattgtt ctggggcttg   4320
tcctcctttc tgttacggtc cagggcaagg tctttgaaag gtgtgagttg gccagaactc   4380
tgaaaagatt gggaatggat ggctacaggg gaatcagcct agcaaactgt aagtctactc   4440
tccataattc cagagaatta gctacgtatg gaacagacac taggagagaa ggaagaagaa   4500 gaagggctt tgagtgaata gatgttttat ttctttgtgg gtttgtatac ttacaatggc    4560
taaaaacatc agtttggttc tttataacca gagatacccg ataaaggaat acgggcatgg   4620
caggggaaaa ttccattcta agtaaaacag gacctgttgt actgttctag tgctaggaag   4680
tttgctgggt gcctgagatt caatggcaca tgtaagctga ctgaaagata catttgagga   4740
cctggcagag ctctctcaag tccttggtat gtgactccag ttatttccca ttttgaactt   4800
gggctctgag agcctagagt gatgcagtat ttttcttgtc ttcaagtccc ctgccgtgat   4860
gtgggatttt tattttatt tttattttat tttatttat tttaaagac agtctcactg       4920 tgtgcccag gctggagtgc agtggcatga ctcagctca ctgcaacctc tgccttctgg      4980
gctcaagtga ttctcgtgct tcagccttct gagtagctgt gactacaggt gtgtaccacc   5040
acacccagct aatttttgt attttcagta gagatgggt tcaccatgt tggccaagct      5100 ggtcttgaac tcctggcctc aaatgatctg cccacctcag cctcccaaag tggtaggatt   5160
acaggtgtga accactgcac ccagccgaca tgggattttt aacagtgatg ttttttaaga   5220
atatattgaa ttccctacac aagagcagta ggaacctagt tcccttcagt cactctttgt   5280
ataggatccc agaaactcag catgaaatgt tttattattt ttatctactc tacttgatta   5340
actatctttc attttctccc acacaattca agatgtgcca tgaggaaaag ttattttata   5400
gtttagtaca tagttgtcga tgtaataatc tctgtagttt tcagattgaa ttcagacatt   5460
tcccctcaat agctattttt gaatgaatga gtgaagggat gaaatcacgg aatagtcttg   5520
ttttcaagat tctaacttga tatccaaatt caccttagaa tattataaga aaatttctat   5580
cagaaaatcc ttatgttttt ctgattaaaa aaagcatttt tccatcagcc tatgtatctg   5640
ctatgaattt acaaaatcta ctcaacagct ctgttgattt ttctgttctt ggctgaatgt   5700
tgcctgaggg atgggagcac gggaagggta aaagcaatgg aagaaacatg tattttaata   5760
```

```
ttttaaaagt atgttatatt gttcgttggt gttacaagat gatttgcatt acaaaaggat    5820
tctcttacaa gtcccttatc ttaacactaa agtgctaaga tattttataa gtaaatcttt    5880
atacttataa aacaaatcag taaaatagaa gtagctaagt agaactgatt ttgctataga    5940
gtataagtca cttagtgttg ctgtttatta ctaaaaataa gttcttttca gggatgtgtt    6000
tggccaaatg ggagagtggt tacaacacac gagctacaaa ctacaatgct ggagacagaa    6060
gcactgatta tgggatattt cagatcaata gccgctactg gtgtaatgat ggcaaaaccc    6120
caggagcagt taatgcctgt catttatcct gcagtggtaa gacaagctaa tatttgacca    6180
atctggttat acttacaaga attgagactc aatacaaatg aaaaagcctt gaaaggttca    6240
tgagggacct agaaaaacta catctcaact tccagaaagt cattattatt ttcctcataa    6300
ttccctgagt aagaaattta agaagtgggt atcataaaag gttgatgttt tttaatatac    6360
agaagtttct ggaatgacct attaatttac tgtcaatggc cttactgatg ctttgtccag    6420
aacaatgcca ttgctcctgc ttactttggg gaggttttgg gataatttag ttgtatggtc    6480
cttttttcaat tgttttactt tttttttttat gaaatgttct aaatgtatag aaaattagag    6540
acattagtat aataaacagc catatgccca ttatgcactt taaaagttgt taacattttg    6600
ccatagttgc ttcttctatg cctttttttt tttttttttt tttttttgct gagagttttt    6660
tgtttggttt tgttttgttt tattttgaga caggtctcc tgtccccagg ctgtagtcag    6720
tggcaccatc acagctcact gcagctcaag tgatcatccc accacagcct cccaagtagc    6780
tgggactaca ggtgtgcacc accatgcctg gcaatttttt gaaatttta gtacaggcaa    6840
attctgtgtt gcccaggctg gtcttgaact cctgagttca agcaatcttc ccacctcagc    6900
ctccttaagc tgctggaatt acaggcgtta gcactgtacc tggctactgc tgagagactt    6960
ttaagtgaat taggaacatg atgatattcc atttctaaat tctttagttt acatcttcaa    7020
aaaatacagt tcctgtagaa ttattattgt aaataacaaa ttaacttaag gatttattta    7080
tttggagtga aacaaatatt ttactgaact cataaaaata gaaataccat gtggaatcct    7140
cagtgtcaaa atattgcag aaatcttgca aagttgatat tattaaattg ttaaatatta    7200
aaattcccaa taaagaacat taatcttatt tctaaaatcc agttaattaa aaaaatttat    7260
attatataat aatatttggt cattaaataa aaattagaaa atacaaataa gaaaaataac    7320
acccataatc ttactaccca gaggtttata accatgggta aattctggta tatattcttc    7380
cagaatgtat atcaatcatg tgtatgaatg ttaaattata tcatacacat ataaacccac    7440
atacaaacat gtaaatactg tgtgcttttg caaaaattaa attgtattat acacgggct    7500
ttacaatttg cttcttatca cacaaaatta tttgcatgtc agcaaataca atcggttttt    7560
taatgatctt ttgctccatt ttccagatga gaaaaaaata caaatctgta tcatcatttt    7620
aaagaatga ctagaatttt aatatatgaa tattctataa tttactgatc caattgttac    7680
tattgagcac ttaggttgtt tccatttttc cctcataaat tgctatgaat agcttttgt    7740
atacatcttt gggtgcattt cttatttctt ttggataaat tttcaataat agaactgctg    7800
agtaaaatat cactaggtgt ttttttacag tgtctagtgc aaagaagacc tttaatcatt    7860
ttgttaatac ttccagagct tccaatgact ttggtaaatg aagaaaaaaa tgcttcattt    7920
catgctgaat gggagagaat gaagagagtt ttccccaaca attacacata tatggactca    7980
tagaaaataa tatcttacca ttcttttccac agcctaacag aaaaaagctg gctaaaccta    8040
aatttaaaat aaaatatcta ttaaagtttt tattccttac cacctgtctt tcagctttgc    8100
tgcaagataa catcgctgat gctgtagctt gtgcaaagag ggttgtccgt gatccacaag    8160
```

-continued

```
gcattagagc atggtatgtt ttaagtgtta aaagggaaaa ctatcttact ctactgttga    8220
tatatacaat gagagcagac ttttaaagac caaagtatgc taatgacacc tcaaaattgc    8280
agcttttggc ttatgctaaa tgatgtatta cctacatcct tgaagaaaca atctacttta    8340
actgatccag aatcttactc ttttactcct caatttattt taggggattt ctagagtttt    8400
aagatgcttc acactctatc agttccttgt catatcttga aattcttttt agaataagta    8460
agtgtgggcc gggcacagtg ctcacgcctg taatcccagc actttgggag accgaggcag    8520
atggatcacc tgaggtcagg agttcgagac cagcctgcct aacatggcaa acccccatct    8580
ccactaaaaa tacaaaaaat tagctgggtg tggtgcaggt gcctgtaatc ccagccactc    8640
gggaggctga ggcaggagac ttgcttgaac ccgggaggtg gaggttgcag aggattgcgc    8700
cattgtactt cagcctgggc gacagagtga gactctgtct caaataaata gcataaaaaa    8760
taaacgtgga attcactttg cagttgctgc tgtacaacgc acattactca atctttatgt    8820
tcggcattct atgctctact gagaaatttg gtaggagtg aagtattttg tatacatatc    8880
ttcatttaat aaatagcaat agctgggtct atcttactat tttatctatt gataaaatat    8940 tttgttccc caaggagtgc gaagtatgta tattacaatg aagatatgtt ttaacctttc    9000
accatttgct tcatcttttt ctacaggtg gcatggagaa atcgttgtca aaacagagat    9060
gtccgtcagt atgttcaagg ttgtggagtg ctcgagggag gaggaggaag cggaggcggc    9120
ggcagcggag gcggaggaag cgctagcatg tgctccaacc tgtccacctg cgtgctgggc    9180
aagctgagcc aggagctgca caagctgcag acctacccta ggaccaacac cggcagcggc    9240
acccctggat aatcgataag cttggatccc ctgccggtgc ctctgggta agctgcctgc    9300 cctgccccac gtcctgggca cacacatggg gtaggggtc ttggtgggc ctgggacccc    9360 acatcaggcc ctgggtcccc cccgtgaga atggctggaa gctgggtcc ctcctggcga    9420 ctgcagagct ggctggccgc gtgcccactc ttgtggggtg acctgtgtcc tggcctcaca    9480
cactgacctc ctccagctcc ttccaggcag agctaagggc taaggtggag gcccaggaag    9540
tgggtaccta aggggaggc taggcgggtc cttctcccga ggaggggctg tcctgaacca    9600
ccagccatgg agaggctggc aagggtctgg caggtgcccc aggaatcaca ggggggcccc    9660
atgtccattt cagggcccgg gagccttggc tcctctgggg acagacgacg tcaccaccgc    9720
ccccccccca tcagggggac tagaagggac caggactgca gtcacccttc ctgggaccca    9780 ggccccctcca ggcccctcct ggggctcctg ctctgggcag cttctccttc accaataaag    9840
gcataaacct gtgctctccc ttctgagtct ttgctggacg acgggcaggg ggtggagaag    9900
tggtggggag ggagtctggc tcagaggatg acagcgggc tgggatccag ggcgtctgca    9960
tcacagtctt gtgacaactg ggggcccaca cacatcactg cggctctttg aaacttttcag   10020 gaaccaggga gggactcggc agagacatct gccagttcac ttggagtgtt cagtcaacac   10080
ccaaactcga caaaggacag aaagtggaaa atggctgtct cttagtctaa taaatattga   10140
tatgaaaact caagttgctc atggatcaaa ttatgccctt ttatgaatcc agccactact   10200
gtcggtatca aacttcatgt acccaaaacg cactgatctt ttctgtgcta aaatgaaata   10260
aagagatttc cccaagatag aggagctggg caaaagaggt cacagttgga aggagacttg   10320
ttctgcacac acagcaagga gatccaacca gttcatccta aaggagatca gtcctgggtg   10380
ttcattggag ggactgatgt tgaagctgaa actccaatgc tttggccacc tgatgtgaag   10440
agctgactca tttgaaaaga ccctgatgct gggaaagatt gagggcagga ggagaagggg   10500
```

```
                                       -continued acgacagagg atgagatggt tggatggcat caccaacaca atggacatgg gtttgggtgg    10560
actccaggag ttggtgatgg acagggaggc ctggcgtgct gcggtttatg gggtcacaaa    10620
gactgagtga ctgaactgag ctgaactgaa tggaaatgag gtatacagca aagtgggggat   10680 tttttagata ataagaatat acacataaca tagtgtatac tcatattttt atgcatacct    10740
gaatgctcag tcactcagtc gtatctgact ctgtgaccta tggaccgtag ccttccaggt    10800
ttcttctgtc cacagaattc tccaggcaag aatactggag tgggtagcca tttcctcctc    10860
caggggatcc tcccgaccca gggattgaac cggcatctcc tgtattggca ggtggattct    10920
ttaccactgt gccaccaggg aagcccgtgt tactctctat gtcccactta attaccaaag    10980
ctgctccaag aaaaagcccc tgtgcctctg agcttcccgg cctgcagagg gtggtggggg    11040
tagactgtga cctgggaaca ccctcccgct tcaggactcc cgggccacgt gacccacagt    11100
cctgcagaca gccgggtagc tctgctcttc aaggctcatt atctttaaaa aaaactgagg    11160
tctattttgt gacttcgctg ccgtaacttc tgaacatcca gtgcgatgga cagcctcctc    11220
cccaggcctc aggggcttca gggagccagc cttcacctat gagtcaccag acactcgggg    11280
gtggccccgc cttcagggtg ctcacagtct tcccatcgtc ctgatcaaag agcaagacca    11340
atgacttctt aggagcaagc agacacccac aggacactga ggttcaccag actgagctgt    11400 cctttgaac ctaaagacac acagctctcg aaggttttct ctttaatctg gatttaaggc    11460
ctacttgccc ctcaagaggg aagacagtcc tgcatgtccc caggacagcc actcggtggc    11520
atccgaggcc acttagtatt atctgaccgc accctggaat taatcggtcc aaactggaca    11580
aaaaccttgg tgggaagttt catcccagag gctcaaccat cctgctttga ccaccctgca    11640 tcttttttc ttttatgtgt atgcatgtat atatatatat atatttttt ttttttcatt      11700 ttttggctgt gctggctgtt cgttgcagtt cggtgcgcag gctttctctc tagtttctct    11760
ctagtcttct cttatcacag agcagtctct agacgatcga cgcgttcagc ctaaagcttt    11820
tttccccgta tcccccagg tgtctgcagg ctcaaagagc agcgagaagc gttcagagga    11880
aagcgatccc gtgccacctt ccccgtgccc gggctgtccc cgcacgctgc cggctcgggg    11940
atgcggggga gcgccggacc ggaccggagc cccgggcggc tcgctgctgc cctagcgggg    12000
gagggacgta attacatccc tgggggcttt ggggggggggc tgtccctgcg gccgcgaatt    12060
c                                                                    12061
```

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Cleavage
      site recognised by enterokinase

<400> SEQUENCE: 5

Phe Pro Thr Asp Asp Asp Lys
  1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Linker arm

<400> SEQUENCE: 6

Gly Gly Gly Gly Ser Gly Gly Gly Gly Ser Gly Gly Gly Gly Ser Ala

```
                1               5              10              15
Ser

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:
      Enterokinase cleavage site

<400> SEQUENCE: 7

Asp Asp Asp Asp Lys
 1               5

<210> SEQ ID NO 8
<211> LENGTH: 15
<212> TYPE: DNA
<213> ORGANISM: Artificial Sequence
<220> FEATURE:
<221> NAME/KEY: CDS
<222> LOCATION: (1)..(15)
<223> OTHER INFORMATION: Description of Artificial Sequence: Normal
      lysozyme C-terminal

<400> SEQUENCE: 8 ggt tgt gga gtg taa                                                    15
Gly Cys Gly Val
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Normal
      lysozyme C-terminal

<400> SEQUENCE: 9

Gly Cys Gly Val
 1

<210> SEQ ID NO 10
<211> LENGTH: 167
<212> TYPE: DNA
<213> ORGANISM: Artificial Sequence
<220> FEATURE:
<221> NAME/KEY: CDS
<222> LOCATION: (1)..(162)
<223> OTHER INFORMATION: Description of Artificial Sequence: C terminal
      extension

<400> SEQUENCE: 10 ctc gag gga gga gga gga agc gga ggc ggc ggc agc gga ggc gga gga        48
Leu Glu Gly Gly Gly Gly Ser Gly Gly Gly Gly Ser Gly Gly Gly Gly
 1               5                  10                  15 agc gct agc atg tgc tcc aac ctg tcc acc tgc gtg ctg ggc aag ctg        96
Ser Ala Ser Met Cys Ser Asn Leu Ser Thr Cys Val Leu Gly Lys Leu
                20                  25                  30 agc cag gag ctg cac aag ctg cag acc tac cct agg acc aac acc ggc       144
Ser Gln Glu Leu His Lys Leu Gln Thr Tyr Pro Arg Thr Asn Thr Gly
            35                  40                  45 agc ggc acc cct gga taa tcgat                                         167
Ser Gly Thr Pro Gly
        50
```

```
<210> SEQ ID NO 11
<211> LENGTH: 53
<212> TYPE: PRT
<213> ORGANISM: Artificial Sequence
<220> FEATURE:
<223> OTHER INFORMATION: Description of Artificial Sequence: C terminal
      extension

<400> SEQUENCE: 11

Leu Glu Gly Gly Gly Gly Ser Gly Gly Gly Gly Ser Gly Gly Gly Gly
 1               5                  10                  15

Ser Ala Ser Met Cys Ser Asn Leu Ser Thr Cys Val Leu Gly Lys Leu
            20                  25                  30

Ser Gln Glu Leu His Lys Leu Gln Thr Tyr Pro Arg Thr Asn Thr Gly
        35                  40                  45

Ser Gly Thr Pro Gly
    50
```